(12) United States Patent
Morgan et al.

(10) Patent No.: US 10,918,657 B2
(45) Date of Patent: Feb. 16, 2021

(54) TREATMENT OF SPINAL CORD INJURY OR TRAUMATIC BRAIN INJURY BY INHIBITION OF SYNUCLEIN PROTEIN AGGREGATION

(71) Applicants: THE REGENTS OF THE UNIVERSITY OF CALIFORNIA, Oakland, CA (US); THE MARINE BIOLOGICAL LABORATORY, Woods Hole, MA (US); BOARD OF REGENTS, THE UNIVERSITY OF TEXAS SYSTEM, Austin, TX (US)

(72) Inventors: Jennifer R. Morgan, Braintree, MA (US); Gal Bitan, Culver City, CA (US); David J. Busch, Manor, TX (US)

(73) Assignees: The Regents of the University of California, Oakland, CA (US); The Marine Biological Laboratory, Woods Hole, MA (US); Board of Regents, The University of Texas System, Austin, TX (US)

( * ) Notice: Subject to any disclaimer, the term of this patent is extended or adjusted under 35 U.S.C. 154(b) by 14 days.

(21) Appl. No.: 14/536,176

(22) Filed: Nov. 7, 2014

(65) Prior Publication Data
US 2015/0202222 A1 Jul. 23, 2015

Related U.S. Application Data

(60) Provisional application No. 61/901,733, filed on Nov. 8, 2013.

(51) Int. Cl.
| | | |
|---|---|---|
| *A61K 31/7088* | (2006.01) | |
| *A61K 31/6615* | (2006.01) | |
| *A61K 31/663* | (2006.01) | |
| *A61K 31/255* | (2006.01) | |
| *A61K 31/194* | (2006.01) | |
| *C12N 15/113* | (2010.01) | |
| *A61K 45/06* | (2006.01) | |

(52) U.S. Cl.
CPC ........ *A61K 31/7088* (2013.01); *A61K 31/194* (2013.01); *A61K 31/255* (2013.01); *A61K 31/663* (2013.01); *A61K 31/6615* (2013.01); *A61K 45/06* (2013.01); *C12N 15/113* (2013.01); *C12N 2310/11* (2013.01); *C12N 2310/3233* (2013.01); *C12N 2310/533* (2013.01)

(58) Field of Classification Search
CPC .............. A61K 31/661; A61K 31/7088; A61K 31/194; A61K 31/255; A61K 31/6615; A61K 31/663; A61K 45/06; C07C 39/17; A61P 25/28; C12N 15/113; C12N 2310/11; C12N 2310/3233; C12N 2310/533
See application file for complete search history.

(56) References Cited

U.S. PATENT DOCUMENTS

| 8,791,092 B2 | 7/2014 | Bitan et al. |
|---|---|---|
| 2012/0108548 A1 | 5/2012 | Bitan et al. |

FOREIGN PATENT DOCUMENTS

| WO | WO 2006/056182 | 6/2006 |
|---|---|---|
| WO | WO 2010/102248 | 9/2010 |

OTHER PUBLICATIONS

Johnson et al. (Nat Rev Neurosci. May 2010 ; 11(5): 361-370).*
PCT International Search Report and Written Opinion dated Sep. 21, 2010 issued in PCT/US2010/026419.
PCT International Preliminary Report on Patentability dated Sep. 6, 2011 issued in PCT/US2010/026419.
EP Office Action dated Dec. 12, 2012 issued in EP10 708 075.6.
EP 2nd Office Action dated Apr. 3, 2014 issued in EP10 708 075.6.
EP 3rd Office Action dated Jul. 9, 2014 issued in EP10 708 075.6.
EP 4th Office Action dated Apr. 20, 2015 issued in EP10 708 075.6.
EP 5th Office Action dated Mar. 22, 2016 issued in EP10 708 075.6.
U.S. Office Action dated Apr. 30, 2013 issued in U.S. Appl. No. 13/203,962.
U.S. Final Office Action dated Nov. 13, 2013 issued in U.S. Appl. No. 13/203,962.
U.S. Notice of Allowance dated Mar. 6, 2014 issued in U.S. Appl. No. 13/203,962.
Branchi et al. (2008) "Fluorescent water-soluble molecular clips. Self-association and formation of adducts in aqueous and methanol solutions" *New Journal of Chemistry* 33(2): 397-407.
Dutt et al. (2013) "Molecular Tweezers with Varying Anions: A Comparative Study" *Journal of Organic Chemistry* 78 (13): 6721-6734.
Fokkens et al. (2005) "A Molecular Tweezer for Lysine and Arginine" Journal of the American Chemical Society 127( 41): 14415-14421.
Fokkens et al. (2005) "Selective Complexation of N-Aikylpyridinium Salts: Binding of NAD+ in Water" *Chem. Eur. J.* 11: 477-494.

(Continued)

*Primary Examiner* — Robert H Havlin
(74) *Attorney, Agent, or Firm* — Tom Hunter; Weaver Austin Villeneuve & Sampson LLP

(57) ABSTRACT

Methods for the treatment of spinal cord injury or traumatic brain injury are provided. In certain embodiments, the methods include the use of a molecular tweezers and/or nucleobase oligomer capable of inhibiting the accumulation or aggregation of one or more amyloidogenic proteins and/or synuclein proteins. Examples of treatments that may inhibit accumulation or aggregation of one or more amyloidogenic proteins and/or synuclein proteins include treatment with a synuclein antisense nucleobase oligomer or treatment with the molecular tweezers CLR01. These treatments may improve outcomes of spinal cord surgery or traumatic brain injury, including, without limitation, neuronal survival, neuronal regeneration, and recovery of neuronal functions.

6 Claims, 14 Drawing Sheets
(11 of 14 Drawing Sheet(s) Filed in Color)
Specification includes a Sequence Listing.

(56) References Cited

OTHER PUBLICATIONS

Gersthagen et al. (2013) "Ditopic Arginine-Aspartate Binders Recognize RGD Loops" *Eur. J. Org. Chem.* 1080-1092.

Gomes et al. (2009) "Host-Guest Interactions between Molecular Clips and Multistate Systems Based on Flavylium Salts" *Journal of the American Chemical Society* 131(25): 8922-8938.

Jasper et al. (2012) "Selective Complexation of N-Alkylpyridinium Salts: Recognition of NAD+ in Water" *Angewandte Chemie. Intl Edition* 41(8):1355-1358.

Kirsch et al. (2009) "A mechanism of efficient G6PD inhibition by a molecular clip" *Angewandte Chemie, Intl. Edition* 48(16): 2886-2890.

Klarner et al. (1996) "Molecular Tweezers as Synthetic Receptors in Host-Guest Chemistry: Inclusion of Cyclohexane and Self-Assembly of Aliphatic Side Chains" *Angewandte Chemie, Intl. Edition* 35(10): 1130-1133.

Klarner et al. (2000) "Molecular tweezers as synthetic receptors: molecular recognition of neutral and cationic aromatic substrates. A comparison between the supramolecular structures in crystal and in solution" *J. Phys. Org. Chem.* 13: 604-611.

Klarner et al. (2003) "Molecular Tweezers and Clips as Synthetic Receptors. Molecular Recognition and Dynamics in Receptor-Substrate Complexes" *Accounts of Chemical Research* 36(12): 919-932.

Klarner et al. (2004) "Effect of Substituents on the Complexation of Aromatic and Quinoid Substrates with Molecular Tweezers and Clips" *Eur. J. Org. Chem.* 1405-1423.

Polkowska et al. (2009) "A combined experimental and theoretical study of the pH-dependent binding mode of NAD+ by water-soluble molecular clips" *Journal of Physical Organic Chemistry* 22(8): 779-790.

Schrader et al. (2005) "Inclusion of Thiamine Diphosphate and S-Adenosylmethionine at Their Chemically Active Sites" *Journal of Organic Chemistry* 70(25): 10227-10237.

Talbiersky et al. (2008) "Molecular Clip and Tweezer Introduce New Mechanisms of Enzyme Inhibition" *Journal of the American Chemical Society* 130(30): 9824-9828.

Blesch, et al., (2009) "Spinal cord injury: plasticity, regeneration and the challenge of translational drug development." *Trends Neurosci.*, 32: 41-47.

Bradbury et al., (2006) "Spinal cord repair strategies: why do they work?" *Nat. Neurosci. Rev.* 7: 644-653.

Busch, et al., (2012) "Synuclein accumulation is associated with cell-specific neuronal death after spinal cord injury." *J. Comp. Neurol.* 520: 1751-1771.

Busch, et. al., (2014) "Acute increase of alpha-synuclein inhibits synaptic vesicle recycling evoked during intense stimulation." *Mol. Biol. Cell* 25: 3926-3941.

Chandra, et al., (2005) "Alpha-synuclein cooperates with CSPalpha in preventing neurodegeneration." *Cell* 123: 383-396.

Cookson, (2009) "alpha-Synuclein and neuronal cell death." *Mol. Neurodegener.* 4: 9 (pp. 1-14).

Cookson, et al., (2008) "Cell systems and the toxic mechanism(s) of alpha-synuclein." *Exp. Neurol.* 209: 5-11.

Ferrucci, et al., (2008) "α-Synuclein and autophagy as common steps in neurodegeneration." *Parkinsonism Relat. Disord.* 14(Suppl. 2): S180-S184.

Fogerson, et al., (2016) "Reducing synuclein accumulation improves neuronal survival after spinal cord injury" *Exp. Neurol.*, 278: 105-115.

Oyinbo (2011) "Secondary injury mechanisms in traumatic spinal cord injury: a nugget of this multiply cascade." *Acta Neurobiol. Exp.* 71: 281-299

Wang, et al., (Apr. 2016) "Knockdown of α-synuclein in cerebral cortex improves neural behavior associated with apoptotic inhibition and neurotrophin expression in spinal cord transected rats." *Apoptosis*, 21(4):404-420.

Sinha et al. (2011) "Lysine-specific molecular tweezers are broad-spectrum inhibitors of assembly and toxicity of amyloid proteins" *J. Am. Chem. Soc.* 133(42): 16958-16969 [NIH Public Access—Author Manuscript—27 pages].

Barbour et al. (2008) "Red Blood Cells Are the Major Source of Alpha-Synuclein in Blood" *Neurodegener. Dis.* 5(2): 55-59.

Bartels et al. (2011) "a-Synuclein occurs physiologically as a helically folded tetramer that resists aggregation" *Nature*, 477(7362): 107-110.

Liu et al. (2018) "Alpha-synuclein in erythrocyte membrane of patients with multiple system atrophy: A pilot study" *Parkinsonism Relat. Disord.* 60: 105-110.

\* cited by examiner

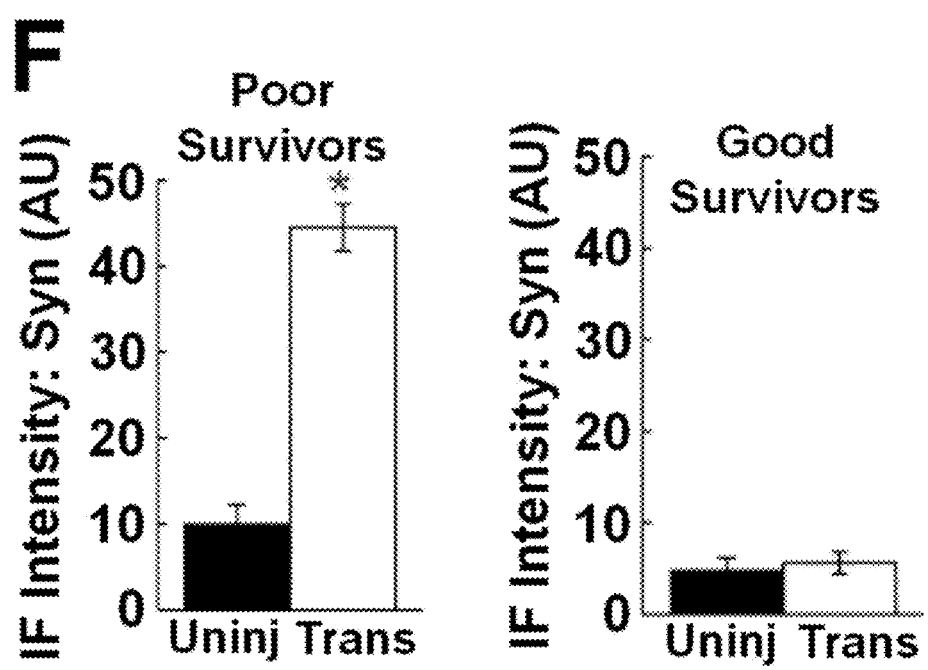
Fig. 1, cont'd.

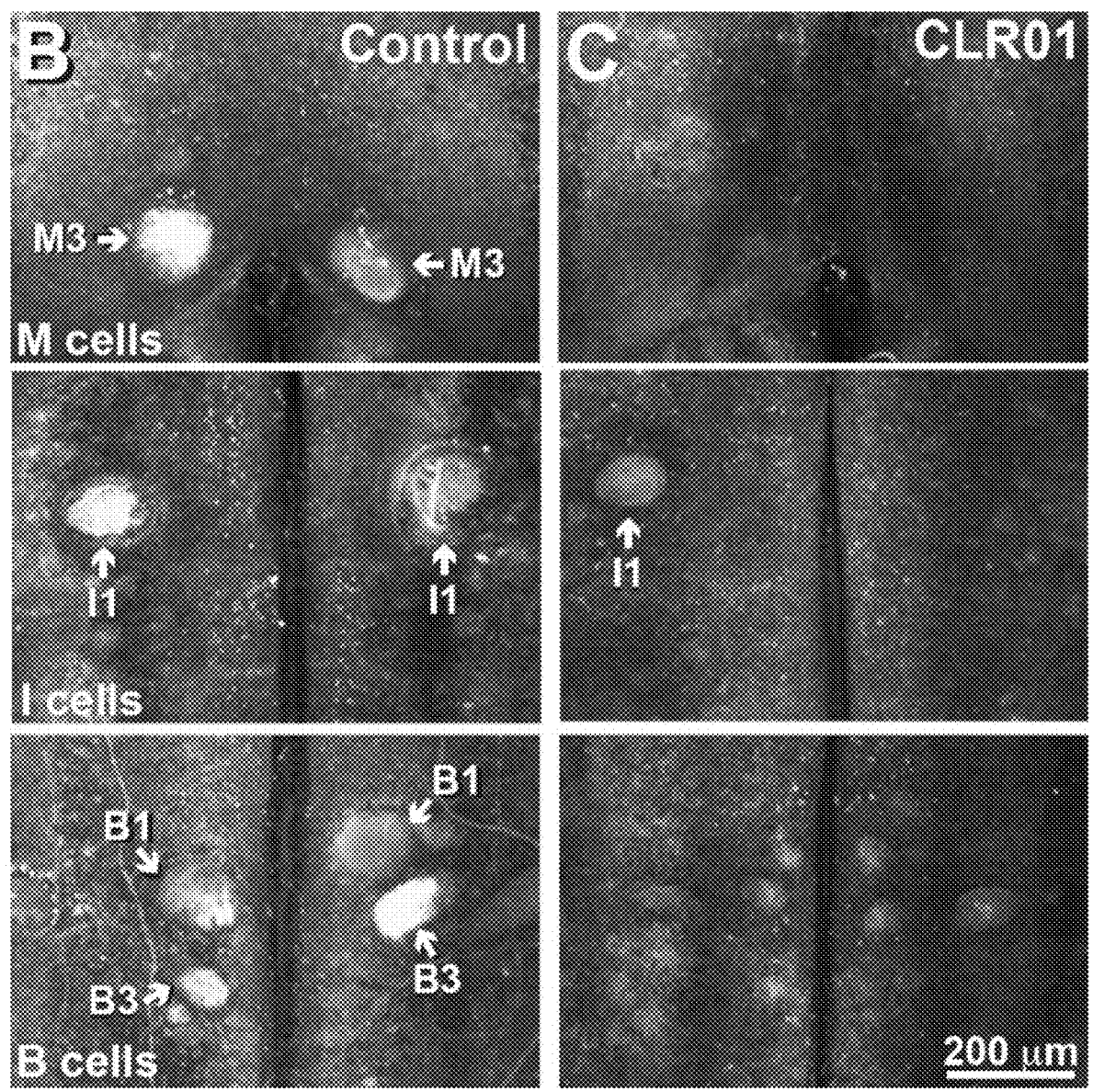
*Fig. 2, cont'd.*

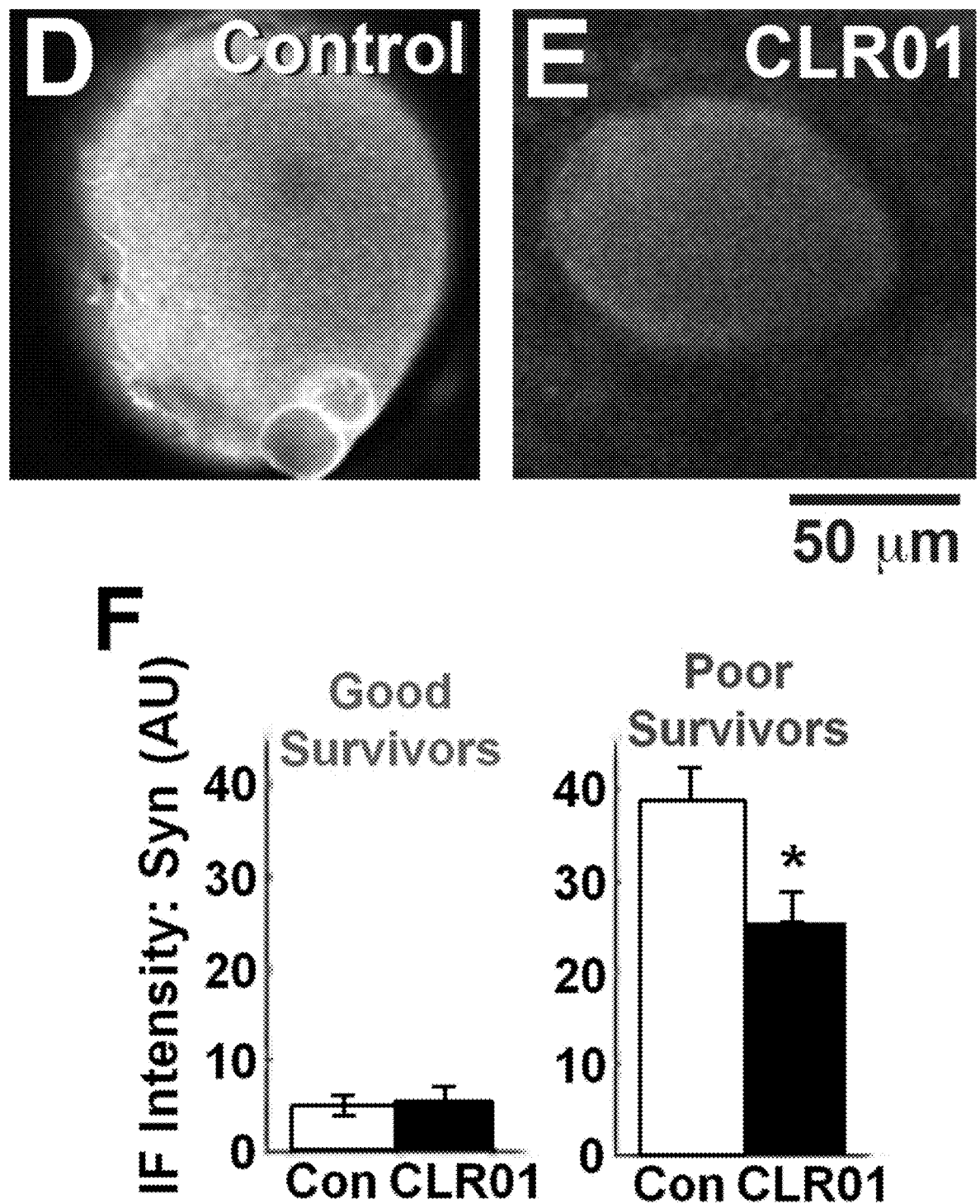
*Fig. 2, cont'd.*

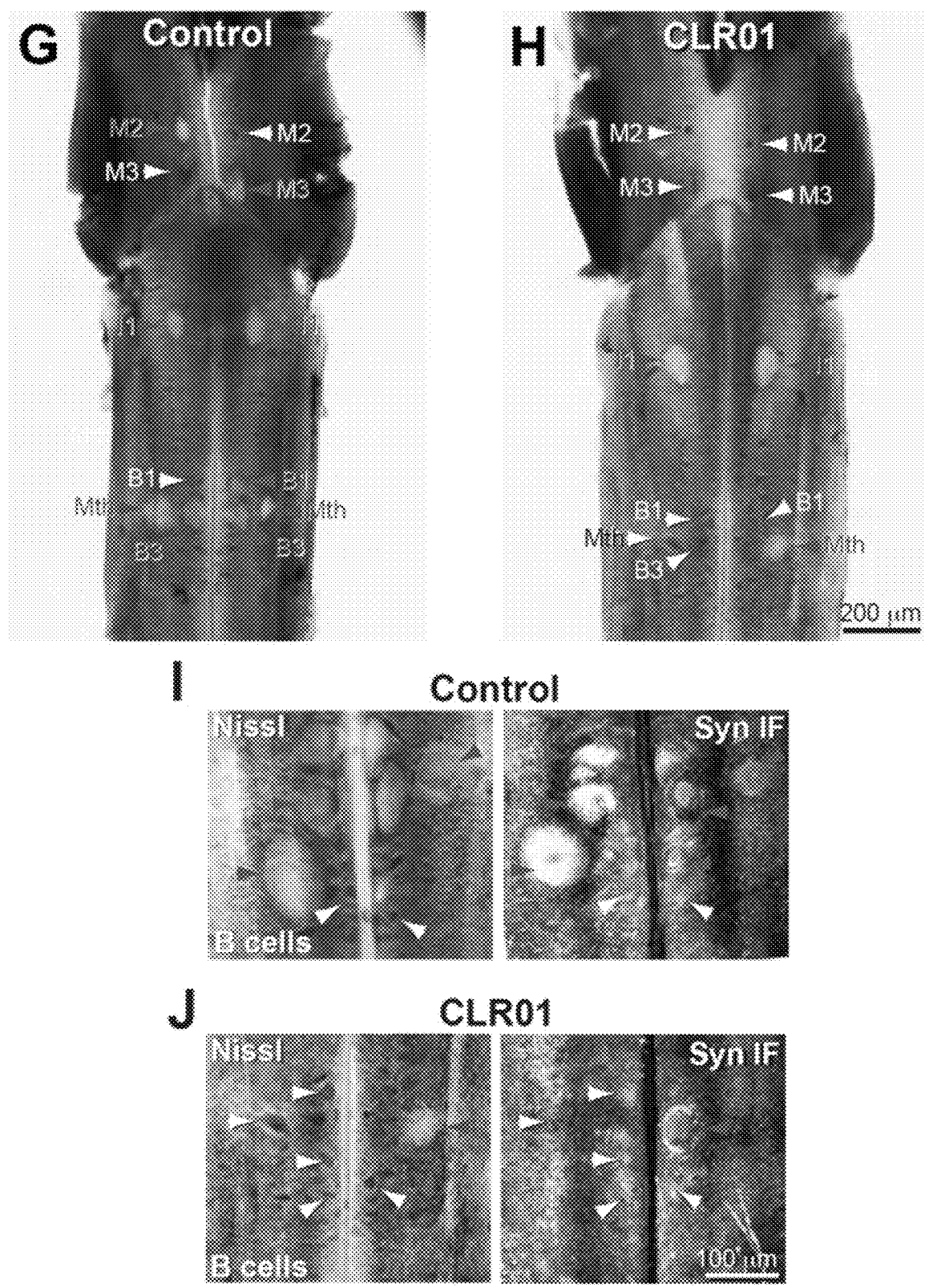
*Fig. 2, cont'd.*

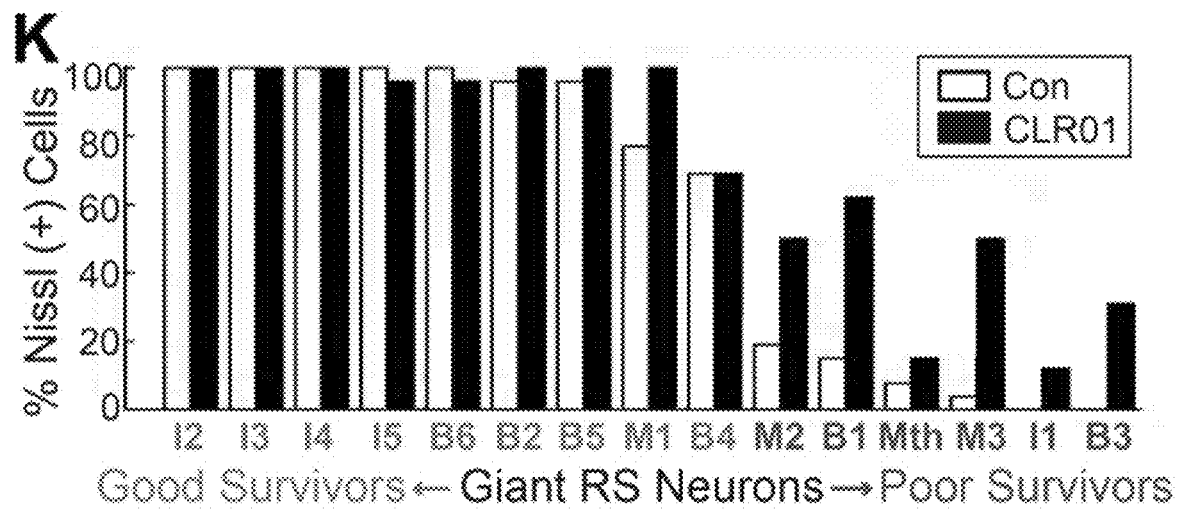
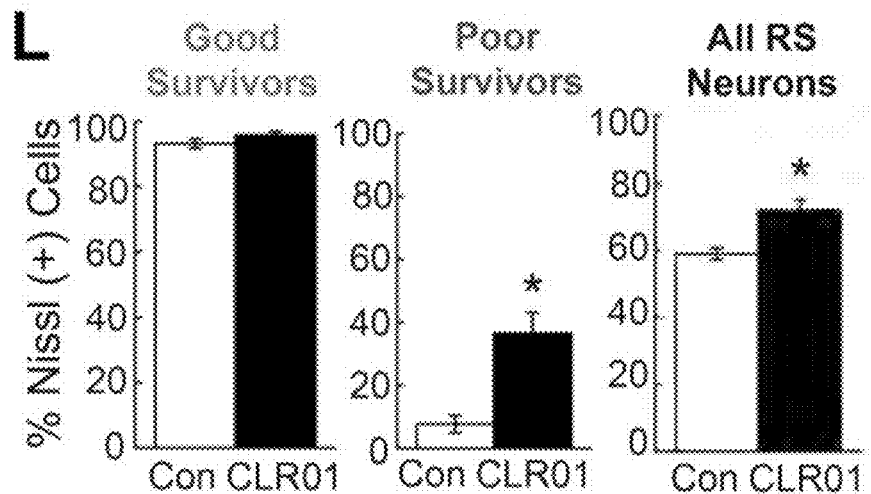
*Fig. 2, cont'd.*

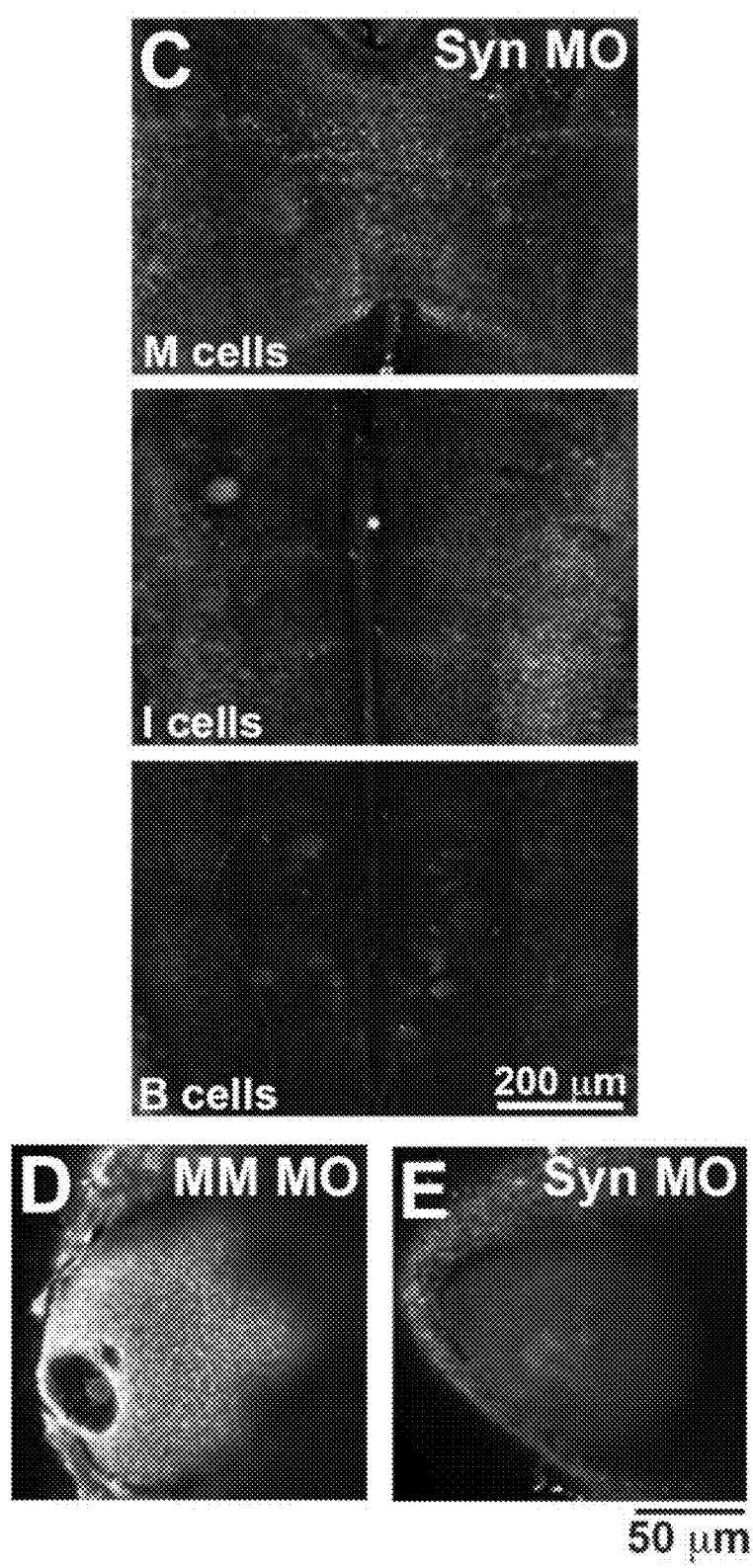
Fig. 3, cont'd.

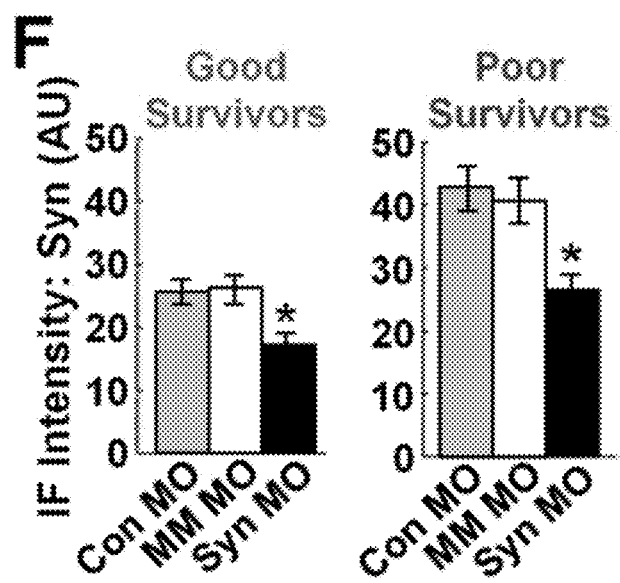
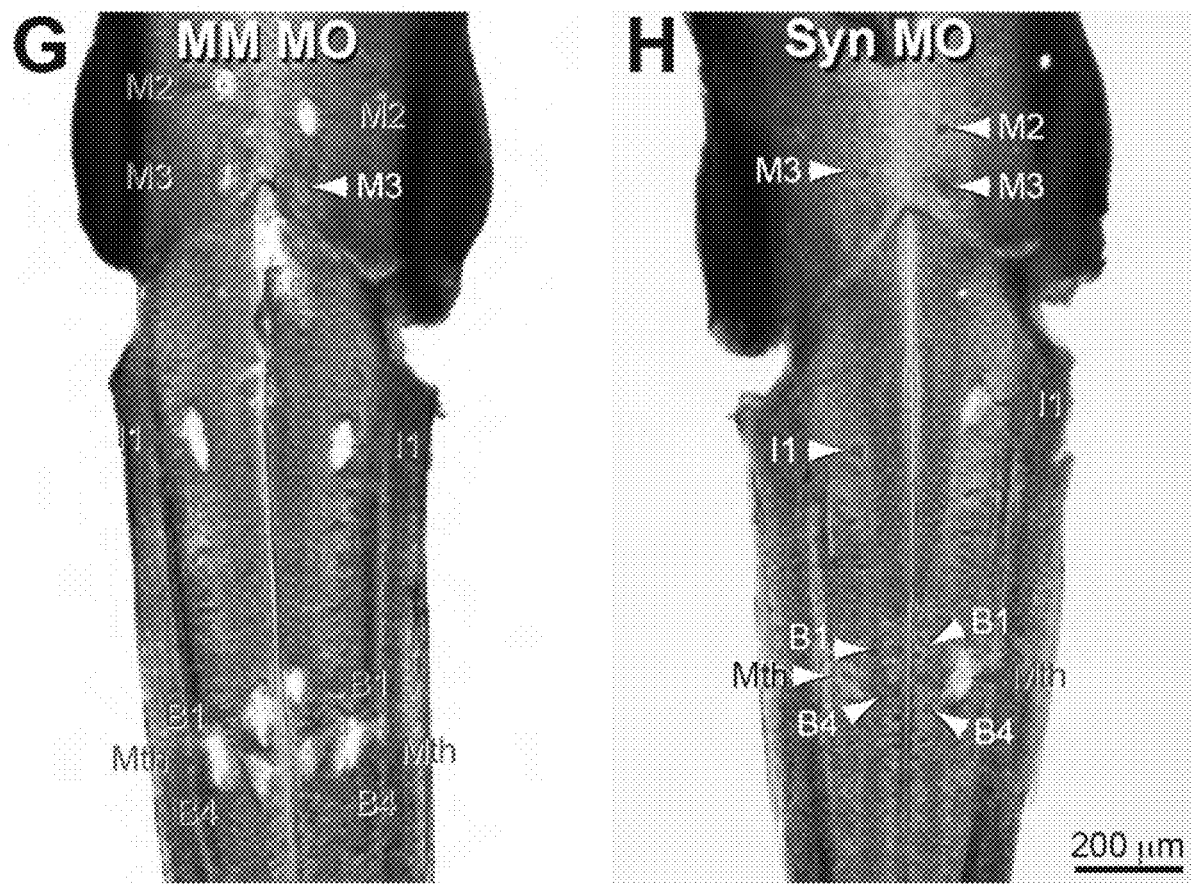
*Fig. 3, cont'd.*

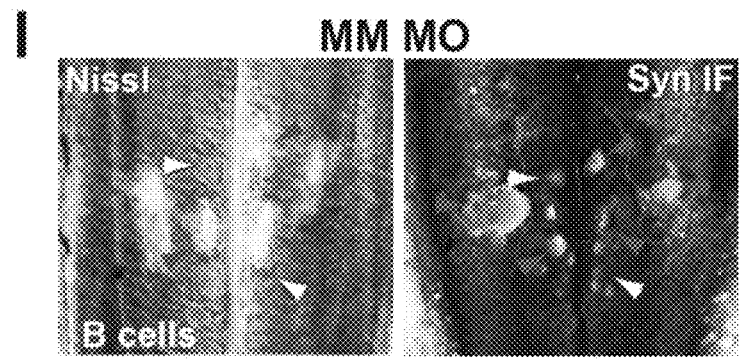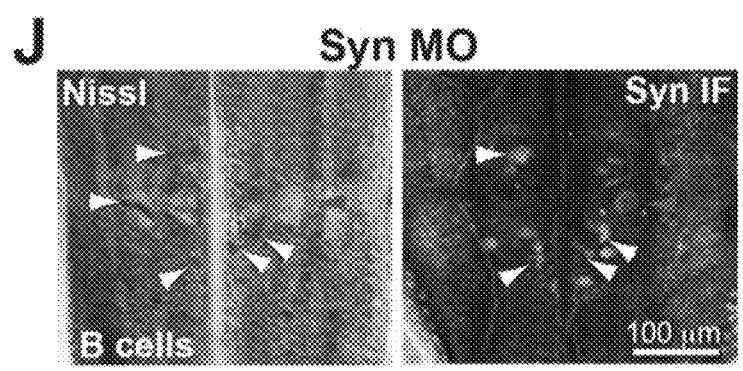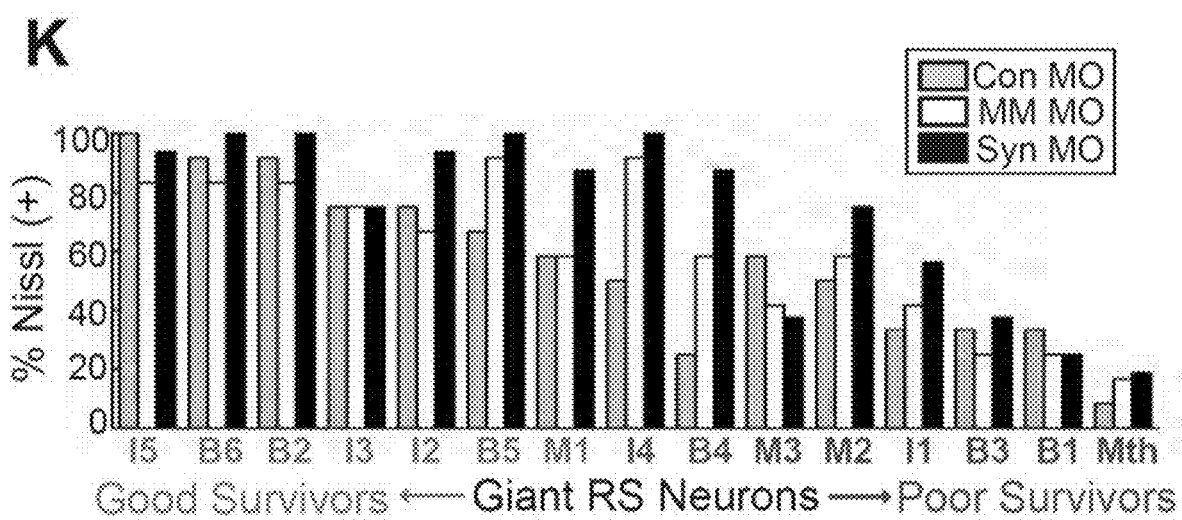
*Fig. 3, cont'd.*

*Fig. 3, cont'd.*

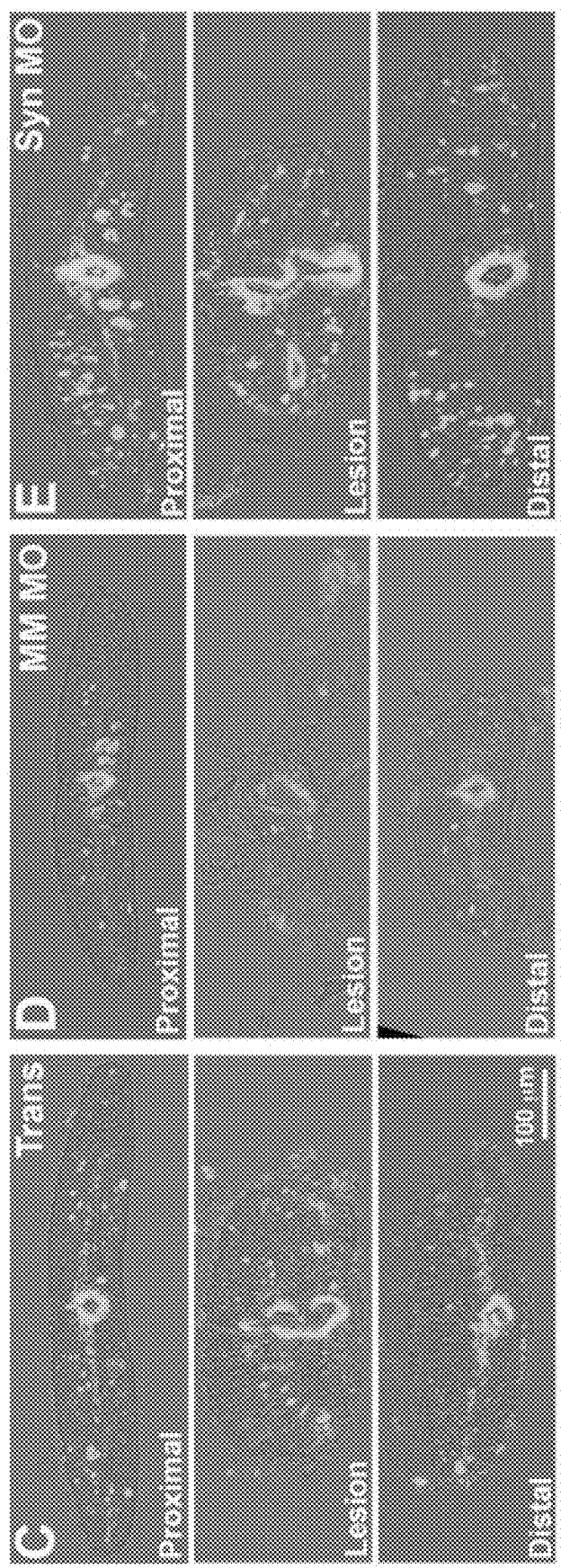
Fig. 4, cont'd.

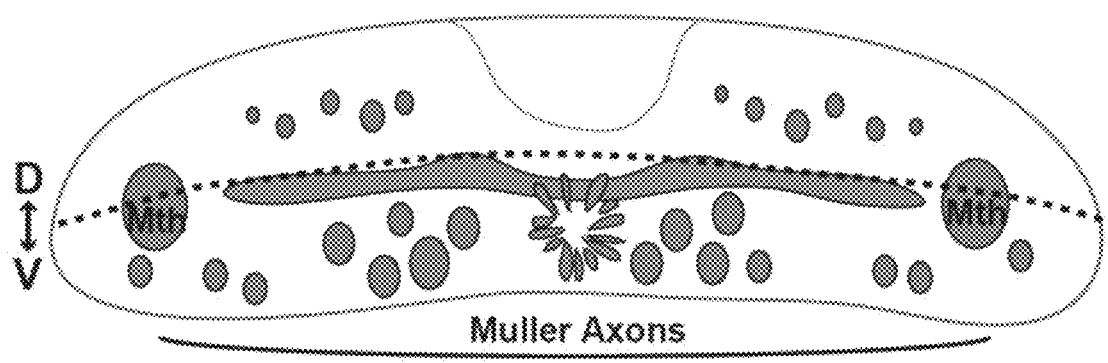
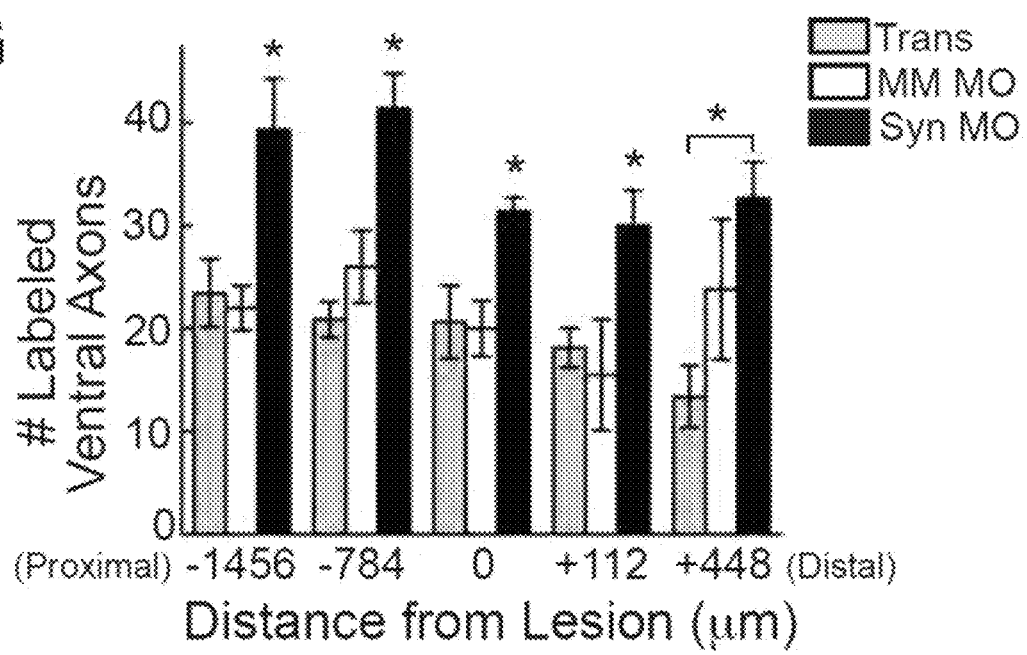
*Fig. 4, cont'd.*

SEQUENCE LISTING

```
<160> NUMBER OF SEQ ID NOS: 6

<210> SEQ ID NO 1
<211> LENGTH: 25
<212> TYPE: DNA
<213> ORGANISM: Homo sapiens

<400> SEQUENCE: 1
aaggaattca ttagccatgg atgta                                    25

<210> SEQ ID NO 2
<211> LENGTH: 25
<212> TYPE: DNA
<213> ORGANISM: Homo sapiens

<400> SEQUENCE: 2
gagtggggcc gccaggatgg acgtg                                    25

<210> SEQ ID NO 3
<211> LENGTH: 25
<212> TYPE: DNA
<213> ORGANISM: Homo sapiens

<400> SEQUENCE: 3
accctgcaca cccaccatgg atgtc                                    25

<210> SEQ ID NO 4
<211> LENGTH: 25
<212> TYPE: DNA
<213> ORGANISM: Artificial
<220> FEATURE:
<223> OTHER INFORMATION: Synthetic oligonucleotide morpholino

<400> SEQUENCE: 4
cgcgtccatt cctctttctt tgtct                                    25

<210> SEQ ID NO 5
<211> LENGTH: 25
```

```
<212> TYPE: DNA
<213> ORGANISM: Artificial
<220> FEATURE:
<223> OTHER INFORMATION: Synthetic oligonucleotide morpholino

<400> SEQUENCE: 5
cgcctgcatt gctctttgtt tctct                                          25

<210> SEQ ID NO 6
<211> LENGTH: 25
<212> TYPE: DNA
<213> ORGANISM: Artificial
<220> FEATURE:
<223> OTHER INFORMATION: Synthetic oligonucleotide morpholino

<400> SEQUENCE: 6
cctcttacct cagttacaat ttata                                          25
```

TREATMENT OF SPINAL CORD INJURY OR TRAUMATIC BRAIN INJURY BY INHIBITION OF SYNUCLEIN PROTEIN AGGREGATION

CROSS-REFERENCE TO RELATED APPLICATIONS

This application claims benefit of and priority to U.S. Ser. No. 61/901,733, filed on Nov. 8, 2013, which is incorporated herein by reference in its entirety for all purposes.

STATEMENT OF GOVERNMENTAL SUPPORT

[Not Applicable]

BACKGROUND

Accumulation, oligomerization, and/or aggregation of amyloidogenic proteins have been associated with cellular dysfunction and cell death. Amyloidogenic proteins are proteins that may participate in amyloidosis, a pathogenic process of protein or peptide misfolding and/or aggregation. Amyloidogenic proteins or peptides may misfold and/or oligomerize to form soluble aggregation intermediates. Amyloidogenic proteins may form fibrils. Oligomers and/or fibrils may contribute to the toxicity of amyloidogenic proteins or peptides. Amyloidogenic proteins or peptides may aggregate to form insoluble amyloid fibers, plaques, or inclusions. A number of diseases, including, but not limited to, Alzheimer's disease (AD), Parkinson's disease (PD), and dementia with Lewy bodies (DLB), have been associated with amyloidogenic proteins and, in some instances, amyloidosis.

Synuclein proteins are a family of soluble proteins common to vertebrates, primarily expressed in neural tissue and in certain tumors. The synuclein proteins include $\alpha$-, $\beta$-, and $\gamma$-synucleins. Synucleins are abundantly expressed and may associate with presynaptic vesicles. Synucleins function, in some instances, in synaptic vesicle trafficking, regulation of soluble N-ethylmaleimide-sensitive factor attachment protein receptor (SNARE) complex formation, or the protection of nerve terminals from neurodegeneration or death. Among the members of this family, $\alpha$-synuclein is generally understood to be an amyloidogenic protein, while $\beta$-synuclein and $\alpha$-synuclein are generally understood to be non-amyloidogenic.

Amyloid $\beta$-protein (A$\beta$) is also an amyloidogenic protein. A$\beta$ may function, in some instances, in neuronal plasticity, learning, memory, or synaptic function. Forms of A$\beta$ may have various lengths, e.g. A$\beta$1-40 and A$\beta$1-42, of which A$\beta$1-42 may have a higher tendency to aggregate and may be the form of A$\beta$ that contributes most to pathogenesis.

Tau is an amyloidogenic protein that may be expressed predominantly in neuronal axons and may associate with microtubules. Functions of Tau may include maintaining the stability of microtubules, promoting microtubule assembly, promoting neurite outgrowth, signaling, nucleolar organization, chromosomal stability, contributions to axonal transport, contributions to axonal function, or contributions to axonal viability. Tau may play an important role in the cellular transport machinery that allows, e.g., signaling molecules, trophic factors, and other essential cellular constituents including organelles (e.g. mitochondria and vesicles) to travel along axons. Multiple isoforms of Tau are known in the art.

Aggregation of Tau may result, e.g., from aberrant phosphorylation or other post-translational modifications of Tau, including acetylation, nitration, oxidation, and truncation, or from an imbalance of Tau isoforms. When the balance between Tau phosphorylation and dephosphorylation is changed in favor of the former, Tau is hyperphosphorylated and the level of the free Tau fraction is elevated. Hyperphosphorylated Tau aggregates into intraneuronal neurofibrillary tangles through oligomers, pretangles (nonfibrillary Tau deposits), and aggregated paired helical filaments. It has also been suggested that oxidative stress could be responsible for detrimental covalent modifications of Tau, which include the formation of intermolecular disulphide bridges, alkylation, and tyrosine nitration. Such modifications are likely to cause misfolding, hyperphosphorylation and aggregation, and thereby contribute to formation of aggregates.

It is unlikely that the full range of medical conditions to which synucleins and other amyloidogenic proteins and peptides contribute has been uncovered. Similarly, it is unlikely that the full range of conditions that may be treated by inhibition or modulation of the accumulation or aggregation of synucleins or other amyloidogenic proteins or peptides has been uncovered.

SUMMARY

In certain embodiments, compositions and methods for the treatment of spinal cord injury and/or traumatic brain injury are provided. In certain particular embodiments, the composition(s) include molecular tweezers and/or a nucleobase oligomer and the treatments involve administering molecular tweezers and/or a nucleobase oligomer.

In certain embodiments, methods of treating a subject having a spinal cord injury and/or traumatic brain injury are provided where the methods comprise administering to the subject a molecular tweezers that inhibits or modulates the aggregation of one or more amyloidogenic proteins and/or non-amyloidogenic synuclein proteins in an amount sufficient to reduce aggregation of the amyloidogenic protein and/or synuclein protein. In particular embodiments, the subject may have a spinal cord injury, a traumatic brain injury, or both. In various embodiments the amyloidogenic protein and/or synuclein protein the aggregation of which is inhibited by the molecular tweezers may be a synuclein protein, a Tau protein, or an A$\beta$ peptide.

In certain embodiments, methods of treating a subject having a spinal cord injury and/or traumatic brain injury are provided where the methods comprise administering to the subject a molecular tweezers that inhibits or modulates the aggregation of an amyloidogenic protein or a synuclein protein in an amount sufficient to ameliorate one or more symptoms of the spinal cord injury or traumatic brain injury. In certain embodiments, the amelioration provides one or more responses selected from the group consisting of improved neuronal survival, improved neuronal regeneration, improvement/recovery of motor function, improvement/recovery of fine motor coordination, improvement/recovery from muscle spasticity, improvement/recovery from paresis or paralysis of one or both sides, reduction in severity and/or number of seizure disorders, improvement/recovery of balance, improvement/recovery of gait, improvement/recovery of cognitive function (e.g., improvement/recovery from short- and long-term memory deficits, improvement/recovery of impaired concentration, improvement/recovery from slowness of thinking and limited attention span), improvement/recovery of perception, improvement/recovery of communication, improvement/recovery of reading and writing skills, improvement/recovery of planning, improvement/recovery of judgment, improvement/recovery of sensory function (e.g., improvement/recovery of hearing, improvement/recovery of sight, improvement/recovery of smell, improvement/recovery of taste).

In certain embodiments, the molecular tweezers used in the methods described herein may be a molecular tweezers according to any one of formulas I to IV:

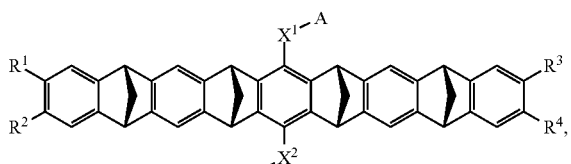

(I)

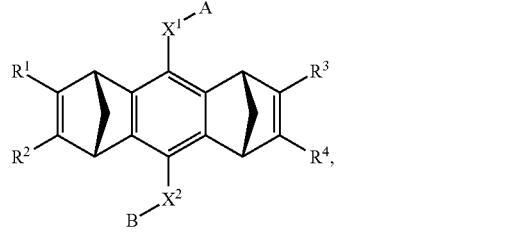

(II)

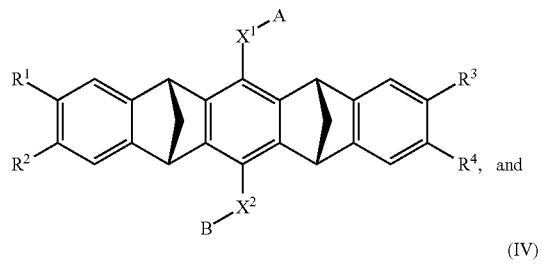

(III)

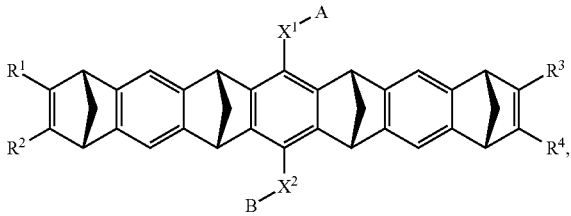

(IV)

or a pharmaceutically acceptable salt, ester, amide, or prodrug thereof, where each of $X^1$ and $X^2$ is O;

A alone, or combined with $X^1$, forms a substituent selected from the group including phosphate, hydrogen phosphate, alkylphosphonate, arylphosphonate, alkylphosphamide, arylphosphamide, sulfate, hydrogen sulfate, alkylcarboxylate, and

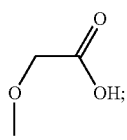

B alone or combined with $X^2$ forms a substituent selected from the group including phosphate, hydrogen phosphate, alkylphosphonate, arylphosphonate, alkylphosphamide, arylphosphamide, sulfate, hydrogen sulfate, alkylcarboxylate and

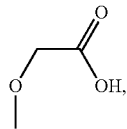

or B is a substituent according to the formula V:

—$X^3$—S—Y—Z        (V)

where:

$X^3$ is absent or is —C(O)—;

S is a spacer;

Y is selected from the group made up of an ester, an amide, a urethane, and a sulfonic ester link; and Z is selected from the group made up of a detectable label, a protein, a nucleic acid, a sugar, and a glycoprotein; and each of $R^1$, $R^2$, $R^3$, and $R^4$ is, independently, selected from the group made up of H, Cl, Br, I, OR, $NR_2$, $NO_2$, $CO_2H$, and $CO_2R^5$, wherein $R^5$ is alkyl, aryl, heteroaryl, or H, or $R^1$ and $R^2$ combine to form an aliphatic or aromatic ring, and/or $R^3$ and $R^4$ combine to form an aliphatic or aromatic ring.

In particular embodiments, the molecular tweezers according to any one of formulas I to IV may be a molecular tweezers according formula I and/or a pharmaceutically acceptable salt, amide, ester, or prodrug thereof, a molecular tweezers according to formula II and/or a pharmaceutically acceptable salt, amide, ester, or prodrug thereof, a molecular tweezers according to formula III and/or a pharmaceutically acceptable salt, amide, ester, or prodrug thereof, and/or a molecular tweezers according to formula IV and/or a pharmaceutically acceptable salt, amide, ester, or prodrug thereof. In certain embodiments, a molecular tweezers according to any one of formulas I to IV may be CLR01, a particular molecular tweezers further described herein. Other molecular tweezers that may be employed in any method of the invention are disclosed in Table 2 of International Publication Number WO 2010/102248 (also published as US 2012/0108548), hereby incorporated by reference for the molecular tweezers described therein. It will be recognized that in certain embodiments a single species of molecular tweezers is administered, while in other embodiments a plurality of species (e.g., 2 or more, or 3 or more, or 4 or more, or 5 or more, etc.) of molecular tweezers are administered.

Administration of molecular tweezers to a subject having a spinal cord injury or a traumatic brain injury may include, but need not be limited to parenteral, intraspinal, intrathecal, epidural, subdural, subcutaneous, intranasal, or intravenous administration. In particular embodiments, administration of a molecular tweezers to a subject having a spinal cord injury or a traumatic brain injury may include administration through a subcutaneously implanted device, or through a surgically implanted cannula.

In any of the above embodiments, molecular tweezers may be administered to a subject having a spinal cord injury or traumatic brain injury within one week of the injury, within 72 hours of the injury, or within 24 hours of the injury.

In certain embodiments, methods for treating a subject having a spinal cord injury or traumatic brain injury may include administering to the subject a nucleobase oligomer, such as a substantially pure nucleobase oligomer, capable of inhibiting synuclein expression. In certain embodiments, the nucleobase oligomer may be up to 30 nucleobases in length and include eight or more consecutive nucleobases complementary to the sequence of one or more synuclein transcripts in the subject. The subject may have, in particular embodiments, a spinal cord injury, a traumatic brain injury, or both.

In any of the above embodiments including a nucleobase oligomer, the eight or more consecutive nucleobases complementary to one or more synuclein transcripts may include a sequence complementary to the start codon of one or more synuclein transcripts. The eight or more consecutive nucleobases complementary to one or more synuclein transcripts may include a sequence complementary to one or more nucleotides 5' of a start codon of one or more synuclein transcripts. In particular embodiments, the eight or more consecutive nucleobases complementary to one or more synuclein transcripts may include a sequence complementary to one or more nucleotides 3' of a start codon of one or more synuclein transcripts. In certain embodiments, a nucleobase oligomer may include 10, 11, 12, 13, 14, 15, 16, 17, 18, 19, 20, 21, 22, 23, 24, 25, 26, 27, 28, 29, or 30 or more consecutive nucleobases complementary to one or more synuclein transcripts.

In certain embodiments a synuclein transcript to which the eight or more consecutive nucleobases are complementary may be an α-synuclein transcript, such as a transcript of a human α-synuclein. In certain embodiments, the eight or more consecutive nucleobases of a nucleobase oligomer may be complementary to the human α-synuclein transcript sequence AAG GAA TTC ATT AGC CAT GGA TGT A (SEQ ID NO:1) or a fragment thereof comprising at least 8 bases. A synuclein transcript to which the eight or more consecutive nucleobases are complementary may be a β-synuclein transcript, such as a transcript of a human β-synuclein. In certain embodiments, the eight or more consecutive nucleobases of a nucleobase oligomer may be complementary to the human β-synuclein transcript sequence GAG TGG GGC CGC CAG GAT GGA CGT G (SEQ ID NO:2) or a fragment thereof comprising at least 8 bases. A synuclein transcript to which the eight or more consecutive nucleobases are complementary may be a β-synuclein transcript, such as a transcript of a human γ-synuclein. In certain embodiments, the eight or more consecutive nucleobases of a nucleobase oligomer may be complementary to the human γ-synuclein transcript sequence ACC CTG CAC ACC CAC CAT GGA TGT C (SEQ ID NO:3) or a fragment thereof comprising at least 8 bases. In certain embodiments, the nucleobase oligomer is a phosphorodiamidate morpholino oligomer.

In certain embodiments, a nucleobase oligomer may be administered to a subject within one week of the injury, within 72 hours of the injury, or within 24 hours of the injury. The nucleobase oligomer may be a phosphorodiamidate morpholino oligomer. In certain embodiments, the nucleobase oligomer may be a peptide nucleic acid (PNA). In certain embodiments the nucleobase oligomer may be a locked nucleic acid (LNA). In certain embodiments the nucleobase oligomer may be an oligonucleotide, such as an oligonucleotide including at least one modified linkage, e.g., a modified linkage selected from the group consisting of phosphorothioate, methylphosphonate, phosphotriester, phosphorodithioate, and phosphoselenate linkages. In some embodiments, the nucleobase oligomer may include at least one modified sugar moiety. The modified sugar moiety may be a 2'-O-methyl group or a 2'-O-methoxyethyl group. In certain embodiments, the nucleobase oligomer may include at least one modified nucleobase. In particular embodiments, the nucleobase oligomer may be admixed with a pharmaceutically acceptable carrier. In certain embodiments administration of the nucleobase oligomer may be oral or may be parenteral, e.g., intraspinal, intrathecal, epidural, subcutaneous, intravenous or through a subcutaneously implanted device.

In various aspects, the invention(s) contemplated herein may include, but need not be limited to, any one or more of the following embodiments:

Embodiment 1

A method of treating a subject having a spinal cord injury or traumatic brain injury, said method including administering to said subject a molecular tweezers that inhibits and/or modulates aggregation of an amyloidogenic protein or a synuclein protein in an amount sufficient to reduce aggregation and/or cytotoxicity of said amyloidogenic protein.

Embodiment 2

A method of treating a subject having a spinal cord injury or traumatic brain injury, said method including administering to said subject a molecular tweezers that inhibits and/or modulates aggregation of an amyloidogenic protein or a synuclein protein in an amount sufficient to ameliorate one or more symptoms of said spinal cord injury or traumatic brain injury.

Embodiment 3

The method of embodiment 2, wherein said amelioration includes one or more responses selected from the group consisting of improved neuronal survival, improved neuronal regeneration, improvement/recovery of motor function, improvement/recovery of fine motor coordination, improvement/recovery from muscle spasticity, improvement/recovery from paresis or paralysis of one or both sides, reduction in severity and/or number of seizure disorders, improvement/recovery of balance, improvement/recovery of gait, improvement/recovery of cognitive function (e.g., improvement/recovery from short- and long-term memory deficits, improvement/recovery of impaired concentration, improvement/recovery from slowness of thinking and limited attention span), improvement/recovery of perception, improvement/recovery of communication, improvement/recovery of reading and writing skills, improvement/recovery of planning, improvement/recovery of sequencing, improvement/recovery of judgment, improvement/recovery of sensory function (e.g., improvement/recovery of hearing, improvement/recovery of sight, improvement/recovery of smell, improvement/recovery of taste).

Embodiment 4

The method of embodiment 2, wherein said amelioration includes amelioration of one or more deficits selected from the group consisting of impairment of sensation, impairment of motor function, dysfunction of the bowel, dysfunction of the bladder, sexual dysfunction, impairment of fertility, inability to effectively regulate blood pressure, impairment of thermoregulation, impairment of sweating, chronic pain, and impairment of involuntary functions (e.g., breathing).

7

Embodiment 5

The method according to any one of embodiments 1-4, wherein said subject has a spinal cord injury.

Embodiment 6

The method according to any one of embodiments 1-4, wherein said subject has a traumatic brain injury.

Embodiment 7

The method of embodiment 6, wherein said traumatic brain injury is caused by an event selected from the group consisting of a falls, a vehicle-related collision, a gunshot wound, domestic violence, child abuse, a sports injury, an explosive blasts, and a combat injuries.

Embodiment 8

The method of embodiment 6, wherein said traumatic brain injury is caused by an ischemic event.

Embodiment 9

The method according to any one of embodiments 1-8, wherein said protein is a synuclein protein.

Embodiment 10

The method according to any one of embodiments 1-8, wherein said amyloidogenic protein is a Tau protein.

Embodiment 11

The method according to any one of embodiments 1-8, wherein said amyloidogenic protein is an Aβ peptide.

Embodiment 12

The method according to any one of embodiments 1-11, wherein said molecular tweezers is a molecular tweezers according to any one of formulas I, II, III, or IV as defined above, or a pharmaceutically acceptable salt, ester, amide, or prodrug thereof.

Embodiment 13

The method of embodiment 12, wherein A and B are independently selected from the group consisting of

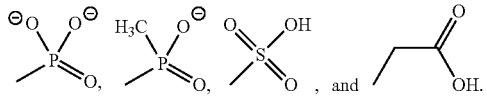

Embodiment 14

The method of embodiments 13, wherein A and B are the same.

Embodiment 15

The method of embodiment 12, wherein A and B are independently selected from the group consisting of

8

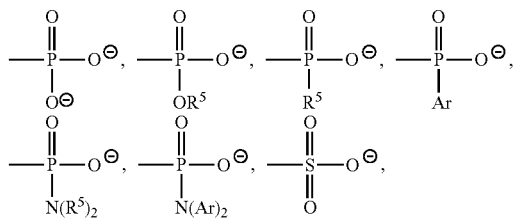

and $-(CH_2)_n-CO_2^-$, where $R^5$ is alkyl or H; n ranges from 1 to 10, and Ar is aryl or heteroaryl.

Embodiment 16

The method of embodiments 15, wherein A and B are the same.

Embodiment 17

The method according to any one of embodiments 12-16, wherein said molecular tweezers is a molecular tweezers according formula I or a pharmaceutically acceptable salt thereof.

Embodiment 18

The method according to any one of embodiments 12-16, wherein said molecular tweezers is a molecular tweezers according formula II or a pharmaceutically acceptable salt thereof.

Embodiment 19

The method according to any one of embodiments 12-16, wherein said molecular tweezers is a molecular tweezers according formula III or a pharmaceutically acceptable salt thereof.

Embodiment 20

The method according to any one of embodiments 12-16, wherein said molecular tweezers is a molecular tweezers according formula IV or a pharmaceutically acceptable salt thereof.

Embodiment 21

The method of embodiment 12, wherein said molecular tweezers is CLR01.

Embodiment 22

The method of embodiment 12, wherein said molecular tweezers is TW2.

Embodiment 23

The method of embodiment 12, wherein said molecular tweezers is TW3.

Embodiment 24

The method of embodiment 12, wherein said molecular tweezers is TW4.

Embodiment 25

The method of embodiment 12, wherein said molecular tweezers is TW5.

Embodiment 26

The method according to any one of embodiments 1-25, wherein said administration is parenteral.

Embodiment 27

The method of embodiment 26, wherein said administration is intraspinal.

Embodiment 28

The method of embodiment 26, wherein said administration is intrathecal or epidural.

Embodiment 29

The method of embodiment 26, wherein said administration is subdural.

Embodiment 30

The method of embodiment 26, wherein said administration is subcutaneous.

Embodiment 31

The method of embodiment 26, wherein said administration is intravenous.

Embodiment 32

The method of embodiment 26, wherein said administration is through a subcutaneously implanted device.

Embodiment 33

The method of embodiment 26, wherein said administration is through a cannula.

Embodiment 34

The method according to any one of embodiments 1-33, wherein said molecular tweezers is administered to said subject within one week of said injury.

Embodiment 35

The method of embodiment 34, wherein said molecular tweezers is administered to said subject within 72 hours of said injury.

Embodiment 36

The method of embodiment 34, wherein said molecular tweezers is administered to said subject within 24 hours of said injury.

Embodiment 37

A method for treating a subject having a spinal cord injury or traumatic brain injury, said method including administering to said subject an effective amount a nucleobase oligomer that inhibits synuclein expression and/or activity, wherein said nucleobase oligomer is up to 30 nucleobases in length and includes eight or more consecutive nucleobases complementary to the sequence of one or more synuclein transcripts in said subject.

Embodiment 38

The method of embodiment 37, wherein said effective amount is an amount effective to inhibit α-synuclein expression.

Embodiment 39

The method according to any one of embodiments 37 and 38, wherein said effective amount is an amount effective to ameliorate a symptom of spinal cord injury and/or traumatic brain injury.

Embodiment 40

The method of embodiment 39, wherein said amount is effective to provide one or more responses selected from the group consisting of improved neuronal survival, improved neuronal regeneration, improvement/recovery of motor function, improvement/recovery of fine motor coordination, improvement/recovery from muscle spasticity, improvement/recovery from paresis or paralysis of one or both sides, reduction in severity and/or number of seizure disorders, improvement/recovery of balance, improvement/recovery of gait, improvement/recovery of cognitive function (e.g., improvement/recovery from short- and long-term memory deficits, improvement/recovery of impaired concentration, improvement/recovery from slowness of thinking and limited attention span), improvement/recovery of perception, improvement/recovery of communication, improvement/recovery of reading and writing skills, improvement/recovery of planning, improvement/recovery of sequencing, improvement/recovery of judgment, improvement/recovery of sensory function (e.g., improvement/recovery of hearing, improvement/recovery of sight, improvement/recovery of smell, improvement/recovery of taste).

Embodiment 41

The method according to any one of embodiments 37-40, wherein said subject has a spinal cord injury.

Embodiment 42

The method according to any one of embodiments 37-40, wherein said subject has a traumatic brain injury.

Embodiment 43

The method of embodiment 42, wherein said traumatic brain injury is caused by an event selected from the group consisting of a falls, a vehicle-related collision, a gunshot wound, domestic violence, child abuse, a sports injury, an explosive blasts, and a combat injuries.

Embodiment 44

The method of embodiment 42, wherein said traumatic brain injury is caused by an ischemic event.

Embodiment 45

The method according to any one of embodiments 37-44, wherein said eight or more consecutive nucleobases complementary to one or more synuclein transcripts comprise a sequence complementary to the start codon of one or more of said transcripts.

Embodiment 46

The method of embodiment 45, wherein said eight or more consecutive nucleobases complementary to one or more synuclein transcripts comprise a sequence complementary to one or more nucleotides 5' of said start codon.

Embodiment 47

The method of embodiment 45 or 46, wherein said eight or more consecutive nucleobases complementary to one or more synuclein transcripts comprise a sequence complementary to one or more nucleotides 3' of said start codon.

Embodiment 48

The method according to any one of embodiments 37-47, wherein said nucleobase oligomer includes 10 or more consecutive nucleobases complementary to said one or more synuclein transcripts or a fragment thereof.

Embodiment 49

The method of embodiment 48, wherein said nucleobase oligomer includes 15 or more consecutive nucleobases complementary to said one or more synuclein transcripts or a fragment thereof.

Embodiment 50

The method of embodiment 49, wherein said nucleobase oligomer includes 20 or more consecutive nucleobases complementary to said one or more synuclein transcripts or a fragment thereof.

Embodiment 51

The method of embodiment 50, wherein said nucleobase oligomer includes 25 or more consecutive nucleobases complementary to said one or more synuclein transcripts or a fragment thereof.

Embodiment 52

The method according to any one of embodiments 37-51, wherein said synuclein transcript is an α-synuclein transcript.

Embodiment 53

The method of embodiment 52, wherein said α-synuclein transcript is a transcript of a human α-synuclein.

Embodiment 54

The method of embodiment 53, wherein said nucleobase oligomer is complementary to the sequence AAGGAATTCATTAGCCATGGATGTA (SEQ ID NO:1) or to a fragment thereof including at least 8 bases.

Embodiment 55

The method according to any one of embodiments 37-51, wherein said synuclein transcript is a β-synuclein transcript.

Embodiment 56

The method of embodiment 55, wherein said β-synuclein transcript is a transcript of a human β-synuclein.

Embodiment 57

The method of embodiment 56, wherein said nucleobase oligomer is complementary to the sequence GAGTGGGGCCGCCAGGATGGACGTG (SEQ ID NO:2) or to a fragment thereof including at least 8 bases.

Embodiment 58

The method according to any one of embodiments 37-51, wherein said synuclein transcript is a γ-synuclein transcript.

Embodiment 59

The method of embodiment 58, wherein said γ-synuclein transcript is a transcript of a human γ-synuclein.

Embodiment 60

The method of embodiment 59, wherein said nucleobase oligomer is complementary to the sequence ACCCTGCACACCCACCATGGATGTC (SEQ ID NO:3) or to a fragment thereof including at least 8 bases.

Embodiment 61

The method according to any one of embodiments 37-60, wherein said nucleobase oligomer is administered to said subject within one week of said spinal cord injury.

Embodiment 62

The method of embodiment 61, wherein said nucleobase oligomer is administered to said subject within 72 hours of said spinal cord injury.

Embodiment 63

The method of embodiment 62, wherein said nucleobase oligomer is administered to said subject within 24 hours of said injury.

Embodiment 64

The method according to any one of embodiments 37-63, wherein said nucleobase oligomer is a phosphorodiamidate morpholino oligomer.

Embodiment 65

The method according to any one of embodiments 37-63, wherein said nucleobase oligomer is an oligonucleotide.

Embodiment 66

The method of embodiment 65, wherein said oligonucleotide includes at least one modified linkage.

Embodiment 67

The method of embodiment 66, wherein said modified linkage is selected from the group consisting of phosphorothioate, methylphosphonate, phosphotriester, phosphorodithioate, phosphoselenate, and peptide linkages.

Embodiment 68

The method according to any one of embodiments 65-67, wherein said nucleobase oligomer includes at least one modified sugar moiety.

Embodiment 69

The method of embodiment 68, wherein said modified sugar moiety is a 2'-O-methyl group or a 2'-O-methoxyethyl group.

Embodiment 70

The method according to any one of embodiments 37-69, wherein said nucleobase oligomer includes at least one modified nucleobase.

Embodiment 71

The method according to any one of embodiments 37-70, wherein said nucleobase oligomer is admixed with a pharmaceutically acceptable carrier.

Embodiment 72

The method according to any one of embodiments 37-71, wherein said administration is oral.

Embodiment 73

The method according to any one of embodiments 37-71, wherein said administration is parenteral.

Embodiment 74

The method of embodiment 73, wherein said administration is intraspinal.

Embodiment 75

The method of embodiment 73, wherein said administration is intrathecal or epidural.

Embodiment 76

The method of embodiment 73, wherein said administration is subdural.

Embodiment 77

The method of embodiment 73, wherein said administration is subcutaneous.

Embodiment 78

The method of embodiment 73, wherein said administration is intravenous.

Embodiment 79

The method of embodiment 73, wherein said administration is through a subcutaneously implanted device.

Embodiment 80

The method of embodiment 73, wherein said administration is through a cannula.

Embodiment 81

A method of treating a subject having a spinal cord injury or traumatic brain injury, said method including administering to said subject: a molecular tweezers that inhibits aggregation of an amyloidogenic protein or a synuclein protein; and a nucleobase oligomer that inhibits synuclein expression and/or activity.

Embodiment 82

The method of embodiment 81, wherein said molecular tweezers is a molecular tweezers as recited in the method of any one of embodiments 12-25.

Embodiment 83

The method according to any one of embodiments 81-82, wherein said nucleobase oligomer is a nucleobase oligomer as recited in any one of embodiments 45-60.

Embodiment 84

The method according to any one of embodiments 81-84, wherein said molecular tweezers is administered before said nucleobase oligomer.

Embodiment 85

The method according to any one of embodiments 81-84, wherein said nucleobase oligomer is administered before said molecular tweezers.

Embodiment 86

The method according to any one of embodiments 81-84, wherein said molecular tweezers and said nucleobase oligomer are administered concurrently.

Embodiment 87

The method of embodiment 86, wherein said molecular tweezers and said nucleobase oligomer are provided in a single formulation.

Embodiment 88

A kit including is a molecular tweezers as recited in the method of any one of embodiments 12-25 and/or a nucleobase oligomer as recited in any one of embodiments 45-60.

Definitions

As used herein, the term "about" means up to +/−10% of the recited value.

The term "subject" is used to refer to a an individual (e.g., a human patient) as well as to a non-human mammal (e.g., canine, feline, porcine, ungulate, canine, lagomorph, non-human primate (for example, a monkey, such as a cynomolus monkey, chimpanzee)). Accordingly, in various embodiments, both human (medical) treatments as well as veterinary applications are contemplated.

The term "traumatic brain injury" (TBI) refers to any microscopic or macroscopic injury, wound, or damage caused by any type of trauma to the head, such as impact to the head or shaking Traumatic brain injury may be an acquired injury to the brain caused by an external physical force. Common causes of traumatic brain injury include, but are not limited to falls (e.g., falling out of bed, slipping in the bath, falling down steps, falling from ladders and related falls), vehicle-related collisions (e.g., collisions involving cars, motorcycles or bicycles, and pedestrians involved in such accidents), violence (e.g., gunshot wounds, domestic violence, or child abuse (e.g., shaken baby syndrome)), sports injuries (e.g., occurring in soccer, boxing, football, baseball, lacrosse, skateboarding, hockey, and other high-impact or extreme sports), explosive blasts and other combat injuries (e.g., from penetrating wounds, severe blows to the head with shrapnel or debris, and falls or bodily collisions with objects following a blast), and the like. Methods for diagnosing TBI are well-established in the art. Traumatic brain injury may also include brain trauma resulting from ischemic events (e.g., stroke), surgery, radiation, or other medical procedures.

The term "spinal cord injury" (SCI) means any microscopic or macroscopic injury, wound, or damage to the spinal cord. Spinal cord injury may be an acquired injury to the spinal cord caused by an external physical force or as the result of a medical condition. Methods for diagnosing spinal cord injury are well-established in the art. Causes of spinal cord injury may include trauma (e.g., by motor vehicle accident, gunshot, falls, etc.), or disease (polio, spina bifida, Friedreich's Ataxia, etc.). Spinal cord injury may be an injury in which the spinal cord is partially or fully severed. Examples of spinal cord injuries in which the spinal cord is not severed may include contusion/bruising or partial transection of the spinal cord. Spinal cord injury may, in certain embodiments, include injuries in which the spinal cord is not severed. SCI includes injuries that occur at various points along the spine, e.g., at or below any of the eight cervical vertebrae or the twelve thoracic vertebrae or at L-I or L-2. Spinal cord injury may also include trauma resulting from surgery, radiation, or other medical procedures.

An "amyloidogenic protein" is a protein or peptide capable of forming an amyloid fiber or a member of a family of proteins or peptides having at least one member capable of forming an amyloid fiber. Amyloidogenic proteins include, without limitation, Tau proteins, Aβ peptides, certain synucleins (e.g., α-synucleins), and the like.

The term "substantially identical" when used with respect to a nucleotide sequence or amino acid sequence means that the sequence has at least 30% identity as compared to a reference sequence, e.g., at least 30%, 40%, 50%, 60%, 70%, 80%, 90%, or 100% identity as compared to a reference sequence. A substantially identical sequence may include one or more sequence changes, deletions, or insertions as compared to the reference sequence. Sequence identity is typically measured using sequence analysis software with the default parameters specified therein, e.g. using Basic Local Alignment Search Tool (BLAST).

A "synuclein protein" means a protein having a sequence substantially identical to the sequence of any member of the synuclein protein family, including an α-, β-, or γ-synuclein protein known in the art. The sequence of one or more synuclein proteins may vary among species, individual organisms, or individual cells.

The term "tau" refers to a protein having a sequence substantially identical to that of a Tau protein known in the art, or a peptide derived there from. The sequence of one or more Tau proteins may vary among species, individual organisms, or individual cells.

The term amyloid β-protein (Aβ) refers to a peptide having a sequence substantially identical that of an Aβ peptide known in the art or a peptide fragment derived therefrom. The sequence of one or more Aβ peptides may vary among species, individual organisms, or individual cells.

The term "endogenous" when used with respect to a polynucleotide, refers to a polynucleotide transmitted to a cell from a parent cell, a polynucleotide expressed from a polynucleotide transmitted to a cell from a parent cell, or a polypeptide expressed from a polynucleotide transmitted to a cell from a parent cell. A portion of an endogenous polypeptide may be referred to as an endogenous peptide.

The term "aggregate" refers to a pathogenic multi-subunit molecular structure including one or more endogenous proteins or peptides. Each subunit of an aggregate may be a protein or peptide. An aggregate may be made up of multiple subunits of a single protein or peptide. An aggregate may be made exclusively of subunits of a single protein or peptide. Alternatively, an aggregate may include one or more subunits of each of two or more proteins or peptides. An aggregate including one or more synuclein proteins, or one or more fragments of one or more synuclein proteins, may be referred to as a synuclein aggregate. An aggregate may be an oligomer, plaque, inclusion, amyloid fiber, or fibril. "Aggregation" means a process leading to the formation of one or more aggregates.

The term "molecular tweezers" refers to one or more noncyclic, rigid, polyaromatic belt-like molecules having open cavities capable of binding one or more guests (e.g., an amyloidogenic protein). The open cavity of a molecular tweezers may bind guests using non-covalent bonding, e.g., hydrogen bonding, metal coordination, hydrophobic forces, van der Waals forces, π-π interactions, or electrostatic effects. A subset of molecular tweezers may include polyaromatic molecular receptors having a structure characterized by two "arms" capable of binding a guest molecule between them.

The term "unmodified", when used with respect to nucleobases, refers to a nucleobase or to a chain of nucleobases comprising only unsubstituted adenine, guanine, cytosine, thymine, and/or uracil nucleotides joined by phosphodiester linkages. A nucleobase oligomer having any other form may be referred to as "modified."

A "nucleobase oligomer" refers to a compound that includes a chain of eight or more nucleobases joined by linkage groups. A nucleobase oligomer may be unmodified or modified. The chain of eight or more nucleobases joined by linkage groups (targeting segment) may be capable of hybridizing to an RNA molecule (i.e., complementary).

The term "expression" refers to the transcription of a gene and/or the translation of a resulting transcript.

The term "inhibit" means to reduce the frequency of occurrence of, number of sites of, and/or severity of a biological process. Inhibition can also include "modulation" of the activity and/or structure of a protein, which, in certain embodiments, can be effected without necessarily affecting the size of the protein. For example, inhibition or modulation of aggregation includes reducing the number or mass of aggregates present in a cell or cells and and/or the levels of an aggregate forming protein in cells, tissues, or circulation. Inhibition may occur through mechanisms including inhibition of aggregate formation and disaggregation of aggregated proteins or peptides. Inhibition may reduce the measured parameter by up to 100%, e.g. by about 1%, 5%, 10%, 20%, 30%, 40%, 50%, 60%, 70%, 80%, 90%, or 100% relative to an untreated control or pretreatment amount.

A "target" of a nucleobase oligomer refers to an RNA molecule having a sequence to which the targeting segment of a nucleobase oligomer is capable of hybridizing, a gene from which the RNA molecule may be transcribed, or a protein that may be translated from the RNA molecule. Accordingly, while a nucleobase oligomer interacts directly with an RNA molecule the target of a nucleobase oligomer may refer to an RNA molecule, a DNA molecule, or a protein. A nucleobase oligomer may be perfectly or imperfectly complementary to an RNA target. A nucleobase oligomer may be referred to as an "antisense nucleobase oligomer" of the target.

The term "knockdown" means to inhibit expression of a target of a nucleobase oligomer. Inhibition of expression of a target may decrease the amount of the target RNA or protein in one or more cells or groups of cells by at least about 1% relative to an untreated control or pretreatment amount. For instance, inhibition of the expression of a target may decrease the amount of the target by at least about 1%, at least about 5%, at least about 10%, at least about 20%, at least about 30%, at least about 40%, at least about 50%, at least about 60%, at least about 70%, at least about 80%, at least about 90%, or about 100% relative to an untreated control or pretreatment amount.

The term "neurodegeneration" refers to the death or impairment of one or more cells of the nervous system.

The term "neurotoxicity" refers to any change within one or more cells that may result in neurodegeneration.

The term "chimeric", when used with respect to a nucleobase oligomer, refers to a nucleobase oligomer that contains two or more chemically distinct segments, each made up of at least one monomer unit. A chimeric nucleobase oligomer may be, for example, an oligonucleotide in which one or more nucleotides of a first segment are chemically distinct form one or more nucleotides of a second segment that does not overlap with the first.

The term "prodrug" refers to a therapeutic agent that is prepared in an inactive form (or a form having reduced or low activity) that may be converted to an active form, or to a form having greater activity, within the body of a subject, e.g. within the cells or tissues of a subject, by the action of one or more enzymes, chemicals, or conditions present with the subject. It will also be recognized that a prodrug need not be inactive. In certain embodiments, prodrugs (active or inactive) can provide one or more other desirable properties including, but not limited to stability, serum half-life, the ability to cross the blood/brain barrier, and the like.

A "pharmaceutically acceptable salt" means a salt that retains the desired biological activity of the parent compound in vivo and does not impart undesired toxicological effects and/or toxicological effects at an undesired level in the organism to which the pharmaceutically acceptable salt form is administered.

The term "purity" means the extent to which a nucleobase oligomer or molecular tweezers, or a pharmaceutical composition thereof, is free of other components. Purity can be expressed as the percentage by weight. A nucleobase oligomer or molecular tweezers may be up to 100% pure, such as at least about 1%, at least about 5%, at least about 10%, at least about 20%, at least about 30%, at least about 40%, at least about 50%, at least about 60%, at least about 70%, at least about 80%, at least about 90%, at least about 95%, at least about 99%, at least about 99.5%, at least about 99.9%, or 100% pure. A composition may be substantially pure if it is at least 20% pure, such as at least about 20%, at least about 30%, at least about 40%, at least about 50%, at least about 60%, at least about 70%, at least about 80%, at least about 90%, at least about 95%, at least about 99%, at least about 99.5%, at least about 99.9%, or 100% pure.

The term "alkyl" means a straight or branched saturated hydrocarbon group having C1 to C14, such as a methyl, ethyl, n-propyl, iso-propyl, n-butyl, sec-butyl, iso-butyl, tert-butyl, etc.

The term "aryl" means an aromatic, unbranched, branched, and/or cyclic, and/or polycyclic hydrocarbon chain. Aryl may include, e.g., a C3-C14, C5-C14, C5-C10, or C5-C6 mono- or poly-cyclic aromatic ring, including, but not limited to, phenyl, naphthyl, and the like. An aryl may be unsubstituted or may have one or more substituent groups. A substituent group can be, e.g., a halogen, C1-6 alkyl, C1-6 halogenoalkyl, C1-6 alkoxy, amino group, or similar group. In various embodiments an aryl may be neutral, positively charged, or negatively charged. Typical aryl groups include, but are not limited to, phenyl, 4-chlorophenyl, 4-fluorophenyl, 4-bromophenyl, 3-chlorophenyl, 3-fluorophenyl, 3-nitrophenyl, 3-(trifluoromethyl)phenyl, 2-methoxyphenyl, 2-methylphenyl, 3-methyphenyl, 4-methylphenyl, 4-ethylphenyl, 2-methyl-3methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl) phenyl and 2-iodo-4-methylphenyl The terms "heteroaryl" or "hetaryl" refer to a substituted or unsubstituted 3-10 membered unsaturated ring containing one, two, three or four heteroatoms, preferably one or two heteroatoms independently selected from oxygen, nitrogen and sulfur or to a bicyclic unsaturated ring system containing up to 10 atoms including at least one heteroatom selected from oxygen, nitrogen and sulfur. Examples of heteroaryls include, but are not limited to, 2-pyridinyl, 3-pyridinyl or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. In certain embodiments the heterocyclic ring may be optionally substituted with up to two substituents.

The term "alkylphosphonate" means a salt of an alkylphosphonic acid anion.

The term "arylphosphonate" means a salt of an arylphosphonic acid anion.

The term "alkylphosphamide" means a salt of a phosphoric acid amide.

The term "arylphosphamide" means a salt of a phosphoric acid aryl amide.

The term "alkylcarboxylate" means a salt of an alkylcarboxylic acid.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
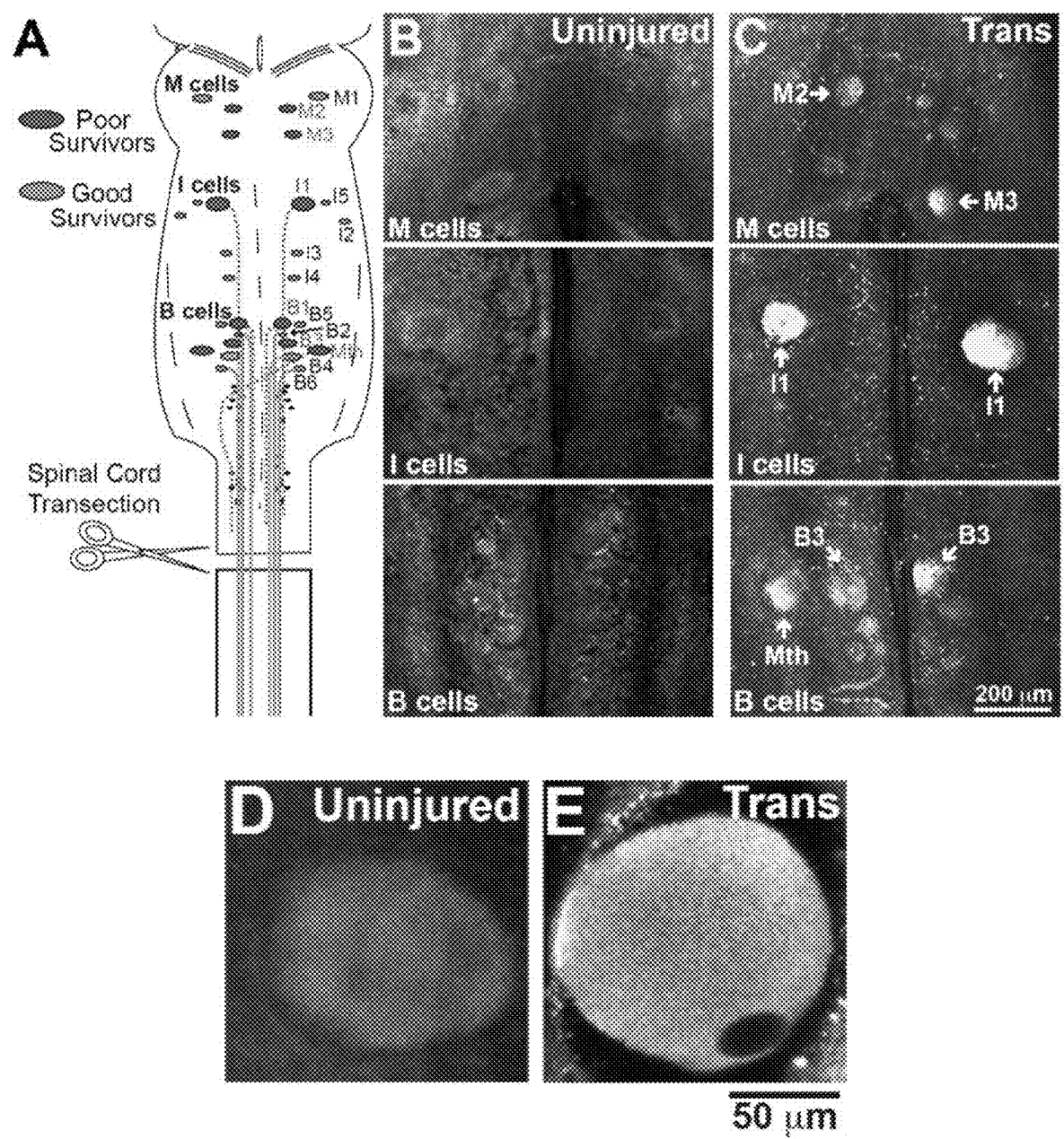
FIG. 1. Post-injury synuclein accumulation in giant RS neurons. Panel A: Diagram of the lamprey brain showing the stereotypical positions of giant RS neurons. After spinal cord transection, the "poor survivors" (red) typically die, whereas "good survivors" (green) survive and regenerate their axons. Panels B-C: Confocal projections showing synuclein immunofluorescence within the mesencephalic (M), isthmic (I) and bulbar (B) cells in the brains of uninjured and transected (Trans) animals. After transection, "poor survivors" preferentially accumulate synuclein. Scale bar in panel C applies to panel B. Panels D-E: Single confocal sections showing low, diffuse levels of synuclein in uninjured neurons and high levels of aggregated synuclein in transected neurons. Scale bar in panel E applies to panel D. Panel F: Synuclein immunofluorescence significantly increases in the "poor survivors" after spinal transection. Bars represent mean±S.E.M. (* $p<0.05$).

Spinal cord injury or traumatic brain injury may result in death or impairment of cells, e.g., neurons and associated loss of function. Death or impairment of cells can negatively impact recovery. For example, neurodegeneration may reduce the potential for recovery of neuronal functions following spinal cord injury or traumatic brain injury. Cells impacted by spinal cord injury or traumatic brain injury may undergo immediate death or impairment or, alternatively, delayed death or impairment. Certain cells may be more likely to die following, e.g., spinal cord injury, than others.

Outcomes of spinal cord injury or traumatic brain injury include, but are not limited to, the impairment or death of cells, e.g. neurons (neurodegeneration). Aspects of neurodegeneration may include decreased neuronal survival, decreased axon sparing, and/or decreased axon growth. Neurodegeneration may limit functional recovery following spinal cord injury or traumatic brain injury or inhibit other post-injury neuronal activities, such as neuronal (e.g., axonal) growth, neuronal (e.g. axonal) regeneration (e.g. axonal sprouting), or neuronal repair. Accordingly, a treatment of spinal cord injury or traumatic brain injury may be a treatment that, without limitation, decreases cellular impairment or cell death (e.g., neurodegeneration), improves functional recovery, and/or improves post-injury neuronal activities.

The various treatments described herein may improve outcomes associated with any of one or more phenotypes or symptoms that may be associated with spinal cord injury or traumatic brain injury. Spinal cord injury or traumatic brain injury may result in a loss of function, such as mobility and/or feeling. SCI may result in, e.g. impairment of sensation, impairment of motor function, dysfunction of the bowel, dysfunction of the bladder, sexual dysfunction, impairment of fertility, inability to effectively regulate blood pressure, impairment of thermoregulation, impairment of sweating, chronic pain, or impairment of involuntary functions (e.g., breathing).

Treatments described herein may improve outcomes associated with any of one or more phenotypes or symptoms that may be associated with traumatic brain injury, including total or partial functional disability, psychosocial impairment, impairment of cognition, impairment of perception, impairment of motor abilities, impairment of physical functions, impairment of information processing, or impairment of speech, impairment of vision, impairment of hearing, sensory impairment; headaches; impairment of fine motor coordination; spasticity of muscles, paresis or paralysis of one or both sides, seizure disorders, impairment of balance; gait impairments, cognitive impairments (e.g., short- and long-term memory deficits, impaired concentration, slowness of thinking and limited attention span, as well as impairments of perception, communication, reading and writing skills, planning, sequencing, and judgment), and psychosocial-behavioral-emotional impairments (e.g., fatigue, mood swings, denial, self-centeredness, anxiety, depression, lowered self-esteem, sexual dysfunction, restlessness, lack of motivation, inability to self-monitor, difficulty with emotional control, inability to cope, agitation, excessive laughing or crying, and difficulty relating to others), chronic or acute pain, and the like.

It was discovered that accumulation of amyloidogenic proteins (including, but not limited to amyloidogenic synucleins (e.g., α-synuclein) and/or non-amyloidogenic synuclein proteins may contribute to outcomes of spinal cord injury or traumatic brain injury, e.g., to the death or impairment of cells, particularly the death or impairment of neurons. It is demonstrated herein that accumulation of amyloidogenic proteins and synuclein proteins in cells following spinal cord injury, and/or aggregation of the accumulated proteins, may contribute to the death of cells. Synuclein proteins may contribute to neurotoxicity and neurodegeneration following spinal cord injury or traumatic brain injury. Without being bound to a particular theory, it is believed that accumulation and aggregation of synuclein proteins, such as α-synuclein, may result in aggregated intracellular inclusions or other intracellular structures, such as amyloid fibers. Alpha-synuclein (α-synuclein), Aβ, Tau, or other amyloidogenic proteins and non-amyloidogenic synuclein proteins known in the art may accumulate and/or aggregate independently following spinal cord injury or traumatic brain injury. Alternatively, any two or more of synuclein proteins and/or amyloidogenic proteins known in the art may accumulate and/or aggregate in an interdependent or correlated manner following spinal cord injury or traumatic brain injury. For instance, cells that accumulate synuclein proteins may also be more prone to accumulate ubiquitin-containing inclusions or to the aggregation of other amyloidogenic proteins, e.g., Aβ or Tau.

Accordingly, compositions and methods for reducing accumulation and/or aggregation of amyloidogenic proteins (including amyloidogenic synuclein proteins) and non-amyloidogenic synuclein proteins following injury, e.g., spinal cord injury or traumatic brain injury are provided. In certain embodiments of the methods described herein, spinal cord injury and/or traumatic brain injury (including, but not limited to acute trauma, ischemia, and the like) is treated by administration of one or more molecular tweezers to the subject (e.g., a human, a non-human mammal, a non-mammalian vertebrate, etc.) having the spinal cord and/or brain injury. In particular embodiments, the molecular tweezers is CLR01, i.e. TW1. In certain embodiments, methods of treating spinal cord injury and/or traumatic brain injury a nucleobase oligomer, e.g., a synuclein antisense nucleobase oligomer are provided. In certain embodiments methods utilizing a combination of molecular tweezers and nucleobase oligomer is contemplated.

Treatment of spinal cord injury and/or traumatic brain injury using the methods described herein can improve survival, regeneration, or other outcomes in cells that are likely to die as a result of injury (e.g., neurons likely to die) and/or cells that are likely to survive injury (e.g., neurons that are likely to survive). Distinct cell types or groups of cells may respond to treatment with varying efficacy or varying responses. Treatment outcomes may also be observed at the systemic or organism level, including some aspects of functional recovery.

Amyloidogenic Proteins and Synuclein Proteins

Expression, accumulation, oligomerization and/or aggregation of amyloidogenic proteins and/or synuclein proteins may negatively impact recovery following spinal cord injury or traumatic brain injury. Neurons may become impaired or die following spinal cord injury or traumatic brain injury, impairing cellular and functional recovery. Accumulation and/or aggregation of amyloidogenic proteins and/or synuclein proteins may contribute to cellular, e.g. neuronal, damage, impairment or death.

Examples of amyloidogenic proteins include, but are not limited to, α-synuclein, Tau, and Aβ. Examples of synuclein proteins are α-synuclein, β-synuclein, and γ synuclein. It is noted that not all synuclein proteins are amyloidogenic. Thus, for example, α-synuclein is known to be amyloidogenic, while β-synuclein and γ-synuclein are generally understood to be non-amyloidogenic. Sequences corresponding to each are known in the art. For example, human synuclein mRNA sequences include, e.g., Accession Numbers NM_000345.3 (α-synuclein), NM_001001502.1 (β-synuclein), and NM_003087 (γ-synuclein). Synucleins are also known in other species, e.g., Lamprey synuclein mRNA sequences include, e.g., Accession Number JN544525.1 (γ synuclein). Human Tau protein mRNA sequences include, e.g., Accession Number NM_016835. Human Aβ precursor protein mRNA sequences include, e.g., NM_000484.

In various embodiments, methods of inhibiting the accumulation or aggregation of amyloidogenic proteins (optionally including α-synuclein) and/or non-amyloidogenic synuclein proteins following spinal cord injury and/or traumatic brain injury are provided. In certain embodiments, such methods include treatment with a molecular tweezers capable of inhibiting accumulation or aggregation of one or more amyloidogenic proteins and/or synuclein proteins and/or treatment with a nucleobase oligomer capable of inhibiting synuclein expression. Examples of treatments to inhibit accumulation or aggregation of one or more amyloidogenic proteins and/or synuclein proteins include treatment with an α-synuclein antisense nucleobase oligomer or treatment with the molecular tweezers CLR01. These treatments may improve outcomes of spinal cord surgery. For instance, treatment with a molecular tweezers or nucleobase oligomer improve neuronal survival, improve axon sparing, improve axon growth, improve neuronal regeneration, improve axon regeneration, or improve axon sprouting. Improved outcomes may occur in the most severely damaged cells, e.g., neurons that are likely to die. Improved outcomes may additionally or alternatively occur in other neurons, such as neurons that are likely to survive. Certain improvements may be observed at the organismal or systemic level. Improvements may occur evenly or unevenly across various cell types, individually identifiable cells, or groups of cells having particular characteristics.

Molecular Tweezers

Molecular tweezer(s) useful in the methods described herein may be capable of inhibiting and/or modulating aggregation of an amyloidogenic protein and/or non-amyloidogenic synuclein proteins, and/or promoting disaggregation of amyloid fibrils or other aggregates of an amyloidogenic protein and/or synuclein protein, or both.

Treatment of spinal cord injury and/or traumatic brain injury with molecular tweezers may improve survival of neurons, and/or regeneration of neurons, and/or other outcomes in cells that are likely to die as a result of injury (e.g., neurons likely to die) and/or cells that are likely to survive injury (e.g., neurons that are likely to survive). Distinct cell types or groups of cells may respond to treatment with molecular tweezers with varying efficacy or varying responses. Treatment outcomes may also be observed at the systemic or organism level, including some aspects of functional recovery.

Examples of molecular tweezers are known in the art, e.g., in International Publication Number WO 2010/102248 (also published as US 2012/0108548), which is herein incorporated by reference in its entirety and, in particular for the molecular tweezers described therein (see, especially Table 2 therein).

Illustrative molecular tweezers useful in the methods described herein may be a molecular tweezers according to any one of Formulas I, II, III, and IV:

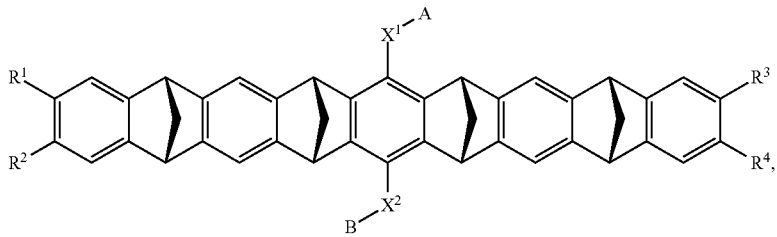
(I)

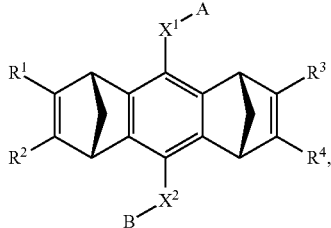
(II)

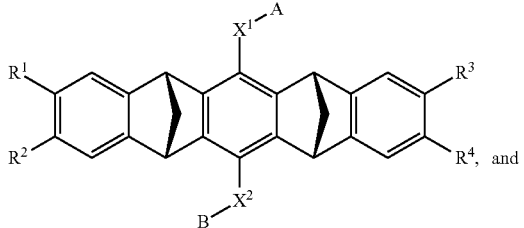
(III)

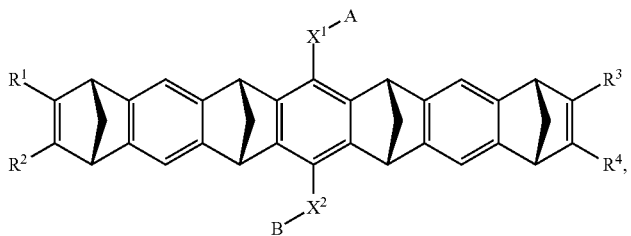
(IV)

or a pharmaceutically acceptable salt thereof, where
each of $X^1$ and $X^2$ is O;

A alone, or A in combination with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

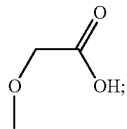

B alone, or B in combination with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

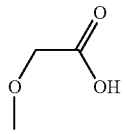

or
B is a substituent according to the formula V:

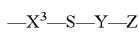  (V)

where:
$X^3$ is absent or is —C(O)—;
S is a spacer;

Y is selected from the group consisting of an ester, an amide, a urethane, and a sulfonic ester link; and Z is selected from the group consisting of a detectable label, a protein, a nucleic acid, a sugar, and a glycoprotein; and each of $R^1$, $R^2$, $R^3$, and $R^4$ is independently selected from the group consisting of H, Cl, Br, I, OR, $NR_2$, $NO_2$, $CO_2H$, and $CO_2R^5$, wherein $R^5$ is alkyl, aryl or H, or $R^1$ and $R^2$ combine to form an aliphatic or aromatic ring, and/or $R^3$ and $R^4$ combine to form an aliphatic or aromatic ring.

In certain embodiments $R^1$, $R^2$, $R^3$, and $R^4$ are all the same.

In certain embodiments, A is a substituent selected from the group consisting of phosphate, hydrogen phosphate, alkylphosphonate, arylphosphonate, alkylphosphamide, arylphosphamide, sulfate, hydrogen sulfate, and alkylcarboxylate.

In certain embodiments, B is a substituent selected from the group consisting of phosphate, hydrogen phosphate, alkylphosphonate, arylphosphonate, alkylphosphamide, arylphosphamide, sulfate, hydrogen sulfate, alkylcarboxylate, or B is a substituent according to the formula V, supra.

In certain embodiments, A and B are independently selected from the group consisting of

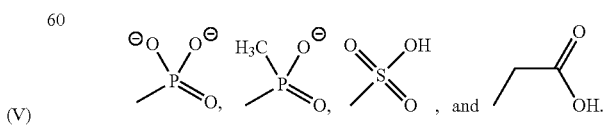

In certain embodiments, A and B are the same, while in other embodiments, A and B are different.

In certain embodiments A alone or A combined with $X^1$ forms a substituent selected from the group consisting of

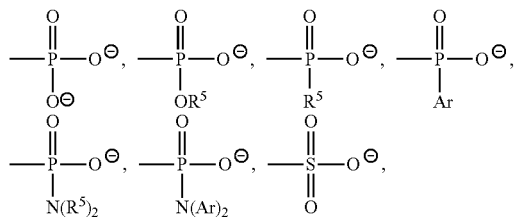

and —$(CH_2)_n$—$CO_2^-$,
where $R^5$ is alkyl or H; n ranges from 1 to 10, and Ar is aryl.

In certain embodiments, B alone or B combined with $X^2$ forms a substituent selected from the group consisting of:

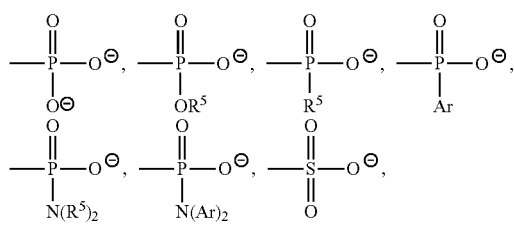

and —$(CH_2)_n$—$CO_2$, where $R^5$ is alkyl or H; n ranges from 1 to 10, and Ar is aryl.

In certain embodiments B includes

-X-Spacer-Y-Fluorescence Dye or the formula

-X-Spacer-Y-Binding site, where
X is a bond or is —(C=O)—, Spacer is a $C_1$-$C_{10}$ alkyl chain, a $C_2$-$C_{10}$ PEG chain, or a $C_1$-$C_{10}$ arylalkyl chain; and where Y is any ester, amide, urethane, or sulfonic acid ester link, such as —(C=O)O—, or —(C=O)NH—, or —O(C=O)—, or —NH(C=O), or —NH—(C=O/S)—NH, —$OSO_2$—, or NH(C=O)O—. In certain embodiments the fluorescent dye may be any commercially available fluorescent dye. The binding site may be any organic fragment. Examples include, but are not limited to:

B = —X-Spacer-Y-Fluorescence Dye;

B = —(C(=O))—Spacer-C(=O)—O/NH-Fluorescence dye;

B = —(C(=O))—Spacer-NH/O—C(=O)-Lys-Leu-Val-Phe-Phe; and

B = —(C(=O))—Spacer-N(H)—C(=O/S)—NH—$C_{10}H_{21}$.

In certain particular embodiments, a molecular tweezers having the formula of TW1 (i.e. CLR01), TW2, TW3, TW4, or TW5 (see formulas below) is used in the methods described herein:

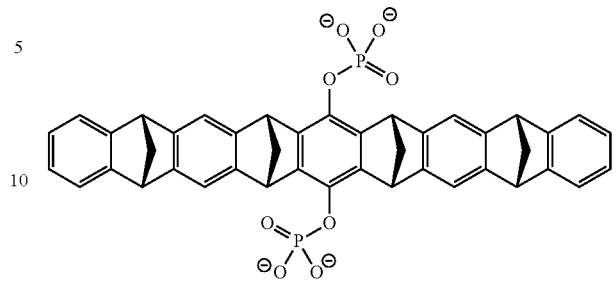

TW1

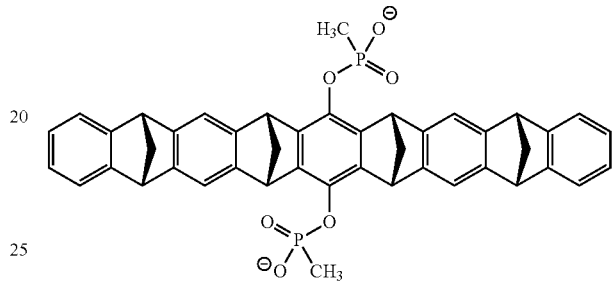

TW2

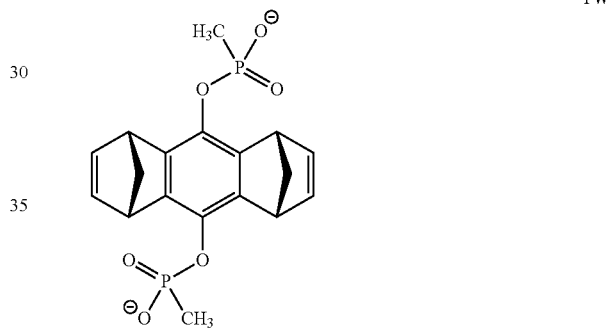

TW3

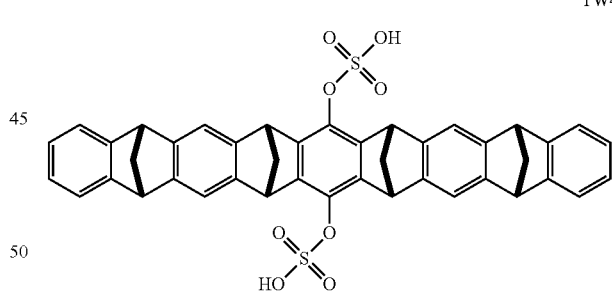

TW4

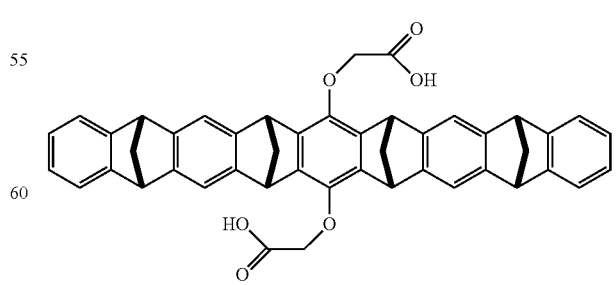

TW5

In particular embodiments one or more of formulas I, II, III, or IV may expressly exclude one or more of a molecular tweezers having the formula of TW1 (i.e. CLR01), TW2, TW3, TW4, or TW5. Other molecular tweezers are known in the art.

Synthesis of Molecular Tweezers

Molecular tweezers may be synthesized according to any of a number of methods known to those of skill in the art (see, e.g., Zimmerman et al. (1991) *J. Am. Chem. Soc.* 113: 183-196). The synthesis of molecular tweezers TW1 (i.e. CLR01), TW2, and TW3 is described below (see also PCT Application No: PCT/US2010/026419).

In one illustrative, but non-limiting embodiment, the skeleton of the tetramethylene-bridged molecular tweezers (the starting material of tweezers TW1 (i.e. CLR01) and TW2) can be constructed by repetitive Diels-Alder reactions of exo-5,6-bismethylene-2,3-benzonorbornene as diene with the bisnorbornadienobenzene as bisdieneophile. Subsequent oxidative dehydrogenation of the cyclohexene rings in the (1:2) Diels-Alder cycloadduct with DDQ leads to the molecular tweezers (Klärner et al. (1999) *Chem. Eur. J.* 5:1700-1707; Klarner et al. (2001) *Tetrahedron*, 57: 3573-3687; Klärner et al. (2004) *Eur. J. Org. Chem.* 7: 1405-1423; Klärner et al. (2008) *Synthesis of molecular tweezers and clips by the use of a molecular Lego set and their supramolecular functions*, Chapter 4:99-153, in *Strategies and Tactics in Organic Synthesis*, Vol. 7 (ed. Harmata, M.), Academic Press, Elsevier, Amsterdam).

The skeleton of the related dimethylene-bridged molecular clips can be synthesized by repetitive Diels-Alder reactions analogously to the synthesis of the tweezers using dibromo-o-quinodimethane derivatives as diene and the same bisdienophile. In this case the HBr elimination in the (1:2) Diels-Alder cycloadduct occurs under the condition of formation leading to the molecular clips in a one-pot reaction.

In one illustrative embodiment, the bisdienophile is the starting material for the synthesis of the tweezers of type TW3. Their preparation starts with a one-pot reaction producing the norbornadienoquinone. The Diels-Alder cycloaddition of 1,3-cyclopentadiene to p-benzoquinone leads to the known (1:1) adduct which isomerizes in the presence of triethylamine to the corresponding hydroquinone that is subsequently oxidized with an excess of p-benzoquinone. The resulting quinone readily reacts with 1,3-cyclopentadiene at −78° C. almost quantitatively leading to a (60:40) mixture of the syn- and anti-Diels-Alder adduct which can be easily separated by recrystallization from toluene. Under basic conditions in the presence of acetic anhydride the syn-adduct is converted to the corresponding diacetoxy-substituted bisdienophile, the starting material of TW3.

The tweezers TW1-3 substituted by methanephosphonate or phosphate groups in the central benzene ring were prepared by reductive or basic ester hydrolysis of the corresponding diacetoxy derivatives followed by esterification of the hydroquinones with MePOCl$_2$ and POCl$_3$, respectively. Hydrolysis and neutralization of the methanephsphonic acid or phosphoric acid derivatives with lithium hydroxide lead to the desired methanephosphonate or phosphate salts (Fokkens et al. (2005) *Chem. Eur. J.* 11: 477-494; Schrader et al. (2005) *J. Org. Chem.* 70:10227-10237; Talbiersky et al. (2008) *J. Am. Chem. Soc.* 130:9824-9828).

Synthesis of TW-2 is described in Fokkens et al. (2005) *J. Am. Chem. Soc.* 27(41): 14415-14421, while the synthesis of various other molecular tweezers (including truncation variants) is described in Klarner et al. (2006) *J. Am. Chem. Soc.* 128(14): 4831-4841. The methods described therein can readily be modified to synthesize other molecular tweezers. These methods may be readily adapted or modified to prepare other molecular tweezers of the present invention.

Formulation and Administration of Molecular Tweezers

In some instances, delivery of a naked, i.e. native form, molecular tweezers may be sufficient to inhibit aggregation of a target protein in a cell. In various embodiments, a molecular tweezers may be administered in the form of a salt, ester, amide, derivative, and the like, provided the salt, ester, amide, or derivative is pharmacologicaly effective (e.g., capable of inhibiting synuclein, Aβ, and/or Tau aggregation). In certain embodiments a prodrug or other adduct or derivative of a compound (e.g., molecular tweezers) described herein which upon administration to a subject in need is capable of providing, directly or indirectly, a compound as otherwise described herein, or a metabolite or residue thereof.

In certain embodiments pharmaceutical compositions are provided, that comprise any one or more of the molecular tweezers described herein (or a prodrug, pharmaceutically acceptable salt, pharmaceutically acceptable ester, pharmaceutically acceptable amide, prodrug, or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a molecular tweezers described herein may be an approved agent to treat the same or related indication, or it may be any one of a number of agents undergoing approval in the Food and Drug Administration for a disorder related to an amyloidogenic process.

Salts, esters, amides, prodrugs and other derivatives of a molecular tweezers can be prepared using standard procedures known in the art of synthetic organic chemistry. For example, in certain embodiments, a pharmaceutically acceptable salt form of the molecular tweezers is contemplated. As used herein, the term "pharmaceutically acceptable salt" refers to those salts that are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, Berge, et al. (1977) *J. Pharmaceutical Sciences*, 66: 1-19, describe pharmaceutically acceptable salts in detail. The salts can be prepared in situ during the final isolation and purification of the active agents (e.g., molecular tweezers), or separately by reacting a free base or free acid function with a suitable reagent, as described generally below. For example, a free base function can be reacted with a suitable acid or a free acid function can be reacted with a suitable free base. Furthermore, where the compounds (such as the molecular tweezers) are or carry an acidic moiety, suitable pharmaceutically acceptable salts thereof may, include metal salts such as alkali metal salts, e.g. sodium, potassium, or copper salts; ammonium hydroxide, calcium hydroxide, trimethylamine, and the like; and alkaline earth metal salts, e.g. calcium or magnesium salts.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certaine embodiments, the compounds described herein are formulated as "p'harmaceuticaly acceptable esters". In certain embodiments suitable esters are esters that hydrolyze in vivo and include those that break down readily in the human body to leave the parent compound or a salt thereof. Suitable ester groups include, but are not limited to, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Preparation of esters may involve functionalization of, e.g., hydroxyl and/or carboxyl groups that are present within the molecular structure of a molecular tweezers. In certain embodiments, the esters are acyl-substituted derivatives of free alcohol groups, i.e., moieties derived from carboxylic acids of the formula RCOOH where R is alky, and preferably is lower alkyl. Esters may be reconverted to the free acids, if desired, by using conventional hydrogenolysis or hydrolysis procedures.

Amides may also be prepared using techniques known in the art. For example, an amide may be prepared from an ester using suitable amine reactants, or prepared from an anhydride or an acid chloride by reaction with ammonia or a lower alkyl amine.

In various embodiments any one or more of the molecular tweezers described herein may be combined with a pharmaceutically acceptable carrier (excipient) to form a pharmacological composition (pharmaceutical formulation). Certain pharmaceutically acceptable carriers can contain one or more physiologically acceptable compound(s) that act, e.g., to stabilize the composition, increase or decrease the absorption of the molecular tweezers, or improve penetration of the blood brain barrier (where appropriate). Physiologically acceptable compounds may include, e.g., carbohydrates (e.g., glucose, sucrose, or dextrans), antioxidants (e.g. ascorbic acid or glutathione), chelating agents, low molecular weight proteins, protection and uptake enhancers (e.g., lipids), compositions that reduce the clearance or hydrolysis of the active agents, or excipients or other stabilizers and/or buffers. Other physiologically acceptable compounds, particularly of use in the preparation of tablets, capsules, gel caps, and the like include, but are not limited to binders, diluents/fillers, disintegrants, lubricants, suspending agents, and the like. In certain embodiments, a pharmaceutical formulation may enhance delivery or efficacy of a molecular tweezers.

In various embodiments, a molecular tweezers described herein may be prepared for parenteral, topical, oral, nasal (or otherwise inhaled), rectal, or local administration. Administration may occur, for example, transdermally, or by aerosol.

A pharmaceutical composition comprising one or more molecular tweezers described herein may be administered in a variety of unit dosage forms depending upon the method of administration. Suitable unit dosage forms, include, but are not limited to, powders, tablets, pills, capsules, lozenges, suppositories, patches, nasal sprays, injectables, implantable sustained-release formulations, and lipid complexes.

In certain embodiments, an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), or an optional lubricant (e.g., talc, magnesium stearate, polyethylene glycol 6000, etc.), may be added to a molecular tweezers and the resulting composition may be compressed to manufacture an oral dosage form (e.g., a tablet). In particular embodiments, a compressed product may be coated, e.g., to mask the taste of the compressed product, to promote enteric dissolution of the compressed product, or to promote sustained release of the molecular tweezers. Suitable coating materials include, but are not limited to, ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds that may be included a pharmaceutical composition comprising one or more molecular tweezers may include wetting agents, emulsifying agents, dispersing agents or preservatives that are particularly useful for preventing the growth or action of microorganisms. Various preservatives are well known and include, for example, phenol and ascorbic acid. The choice of pharmaceutically acceptable carrier(s), including a physiologically acceptable compound, depends, e.g., on the route of administration of the molecular tweezers and on the particular physio-chemical characteristics of the molecular tweezers.

In certain embodiments, one or more excipients for use in a pharmaceutical composition including one or more molecular tweezers may be sterile and/or substantially free of undesirable matter. Such compositions may be sterilized by conventional techniques known in the art. For various oral dosage form excipients, such as tablets and capsules, sterility is not required. Standards are known in the art, e.g., the USP/NF standard.

A pharmaceutical composition comprising one or more molecular tweezers as described herein may be administered in a single or in multiple administrations depending on the dosage, the required frequency of administration, and the known or anticipated tolerance of the subject for the pharmaceutical composition with respect to dosages and frequency of administration. In various embodiments, the composition may provide a sufficient quantity of a molecular tweezers to effectively treat (ameliorate one or more symptoms of) spinal cord injury or traumatic brain injury in the subject (e.g., decrease cellular impairment or cell death (e.g., neurodegeneration), improve functional recovery, and/or improve post-injury neuronal activities).

In some embodiments, a molecular tweezers may be administered within one week of a spinal cord injury or traumatic brain injury or before, during or after the onset of a neurodegenerative process. In particular embodiments, a molecular tweezers may be administered within 3 days (72 hours) of a spinal cord injury or traumatic brain injury. In still more particular embodiments, a molecular tweezers may be administered within 1 day (24 hours) of spinal cord injury or traumatic brain injury.

The amount and/or concentration of molecular tweezers to be administered to a subject may vary widely, and will typically be selected primarily based on activity of the molecular tweezers and the characteristics of the subject, e.g., species and body weight, as well as the particular mode of administration and the needs of the subject. In certain embodiments, the dosage of molecular tweezers may be 0.001 to about 50 or more mg/kg/day. For example, the dosage of a molecular tweezers may be about 0.001, 0.01, 0.1, 1, 5, 10, 20, 30, 40, or 50 or more mg/kg/day. In certain embodiments typical dosages range from about 1 mg/kg/day to about 3 mg/kg/day, from about 3 mg/kg/day to about 10 mg/kg/day, from about 10 mg/kg/day to about 20.0 mg/kg/day, or from about 20 mg/kg/day to about 50 mg/kg/day. In certain embodiments, dosages range from about 10 mg/kg/day to about 50 mg/kg/day. In certain embodiments, dosages range from about 20 mg to about 50 mg given orally twice daily. Dosages may be varied to optimize a therapeutic and/or prophylactic regimen in a particular subject or group of subjects.

In certain embodiments, a molecular tweezers of the present invention is administered to the oral cavity, e.g., by the use of a lozenge, aersol spray, mouthwash, coated swab, or other mechanism known in the art.

In certain embodiments a molecular tweezers of the present invention may be administered systemically (e.g., orally, or as an injectable) in accordance with standard methods known in the art. In certain embodiments, the molecular tweezers may be delivered through the skin using a transdermal drug delivery systems, i.e., transdermal "patches," wherein the molecular tweezers are typically contained within a laminated structure that serves as a drug delivery device to be affixed to the skin. In such a structure, the drug composition is typically contained in a layer, or reservoir, underlying an upper backing layer. The reservoir of a transdermal patch includes a quantity of molecular tweezers that is ultimately available for delivery to the surface of the skin. Thus, the reservoir may include, e.g., the molecular tweezers of the present invention in an adhesive on a backing layer of the patch, or in any of a variety of different matrix formulations known in the art. The patch may contain a single reservoir or multiple reservoirs.

In one particular transdermal patch embodiments, a reservoir may comprise a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, and polyurethanes. Alternatively, the molecular tweezers-containing reservoir and skin contact adhesive are present as separate and distinct layers, with the adhesive underlying the reservoir which, in this case, may be either a polymeric matrix as described above, a liquid or hydrogel reservoir, or another form of reservoir known in the art. The backing layer in these laminates, which serves as the upper surface of the device, preferably functions as a primary structural element of the patch and provides the device with a substantial portion of flexibility. The material selected for the backing layer is preferably substantially impermeable to the molecular tweezers and to any other materials that are present.

Additional formulations for topical delivery include, but are not limited to, ointments, gels, sprays, fluids, and creams. Ointments are semisolid preparations that are typically based on petrolatum or other petroleum derivatives. Creams including a molecular tweezers are typically viscous liquids or semisolid emulsions, e.g. oil-in-water or water-in-oil emulsions. Cream bases are typically water-washable and include an oil phase, an emulsifier, and an aqueous phase. The oil phase, also sometimes called the "internal" phase, of a cream base is generally comprised of petrolatum and a fatty alcohol, e.g. cetyl alcohol or stearyl alcohol; the aqueous phase usually, although not necessarily, exceeds the oil phase in volume, and generally contains a humectant. The emulsifier in a cream formulation is generally a non-ionic, anionic, cationic, or amphoteric surfactant. The specific ointment or cream base to be used may be selected to provide for optimum drug delivery according to the art. As with other carriers or vehicles, an ointment base may be inert, stable, non-irritating, and non-sensitizing.

Various buccal and sublingual formulations are also contemplated.

In certain embodiments, administration of a molecular tweezers of the present invention may be parenteral. Parenteral administration may include, for example, intraspinal, intrathecal, epidural, subdural, subcutaneous, or intravenous administration. Means of parenteral administration are known in the art. In particular embodiments, parenteral administration may include a subcutaneously implanted device.

In certain embodiments, it may be desirable to deliver the molecular tweezers to the brain. In embodiments including system administration, this could require that the molecular tweezers cross the blood brain barrier. In various embodiments this may be facilitated by co-administering a molecular tweezers with carrier molecules such as cationic dendrimers or arginine-rich peptides, which may carry a molecular tweezers over the blood brain barrier.

In certain embodiments a molecular tweezers may be delivered directly to the brain by administration through the implantation of a biocompatible release system (e.g., a reservoir), by direct administration through an implanted cannula, by administration through an implanted or partially implanted drug pump, or mechanisms of similar function known the art. In certain embodiments, a molecular tweezers may be systemically administered (e.g., injected into a vein). In certain embodiments it is expected that the molecular tweezers will be transported across the blood brain barrier without the use of additional compounds included in a pharmaceutical composition to enhance transport across the blood brain barrier.

In certain embodiments, one or more active agents of the present invention may be provided as a concentrate, e.g., in a storage container or soluble capsule ready for dilution or addition to a volume of water, alcohol, hydrogen peroxide, or other diluent. A concentrate of the present invention may be provided in a particular amount of molecular tweezers and/or a particular total volume. The concentrate may be formulated for dilution in a particular volume of diluents prior to administration.

Other suitable formulations and modes of administration are known or may be derived from the art.

A molecular tweezers of the present invention may be administered to a mammal in need thereof, such as a mammal diagnosed as having or at risk for a medical condition characterized by amyloidogenic protein aggregation, e.g., spinal cord injury. A molecular tweezers of the present invention may be administered to inhibit aggregation of one or more amyloidogenic proteins, e.g. synuclein, Aβ, or Tau. A molecular tweezers of the present invention may be administered to mitigate one or more symptoms of spinal cord injury or traumatic brain injury.

A therapeutically effective dose of a pharmaceutical composition of the present invention may depend upon the age of the subject, the gender of the subject, the species of the subject, the particular pathology, the severity of the symptoms, and the general state of the subject's health.

In certain therapeutic or prophylactic applications, molecular tweezers described herein may be administered to a mammal (e.g., to a non-human mammal or to a human, e.g., to a human having or at risk of a spinal cord injury) to prophylactically and/or therapeutically inhibit synuclein, Aβ, or Tau aggregation, and/or to slow the onset, and/or to slow the progression, and/or to mitigate one or more symptoms of a spinal cord injury or traumatic brain injury, including but not limited to synuclein, Aβ, or Tau aggregation. It will be recognized that prophylactic treatment requires identification of a subject at heightened risk for traumatic brain injury and/or spinal cord injury. Such subjects include, but are not limited to football players, boxers, and subjects contemplating medical procedures (e.g., surgery and/or radiation) that can damage brain and/or spinal cord tissue.

The pharmaceutical compositions described herein may be suitable for administration to an animal, e.g., for veterinary use. Certain embodiments of the methods described herein may include administration of a pharmaceutical composition of the present invention to a non-human organisms, e.g., non-human mammals such as a non-human primates, canine, equine, feline, porcine, ungulate, lagomorphs, or other vertebrates. In various embodiments the pharmaceutical compositions are suitable for administration to a human.

Nucleobase Oligomers

In various embodiments nucleobase oligomers, e.g., oligonucleotides, that inhibit accumulation or aggregation of one or more amyloidogenic proteins, and their use in the treatment of spinal cord injury or traumatic brain injury (including, but not limited to acute trauma, ischemic events (e.g., stroke)) are provided. Suitable nucleobase oligomers may include a chain of eight or more nucleobases capable of hybridizing to a target RNA molecule. In particular embodiments, a suitable nucleobase oligomer may include 8, 9, 10, 11, 12, 13, 14, 15, 20, 25, or 30 nucleobases capable of hybridizing to a target RNA molecule. The target RNA molecule may be, e.g., an RNA transcript encoding a synuclein protein, a Tau protein, or an Aβ peptide. In particular embodiments, a synuclein protein, Tau protein, or Aβ peptide targeted by a nucleobase oligomer may be a human synuclein protein, Tau protein, or Aβ peptide. In certain embodiments, a suitable nucleobase oligomer may target a human α-synuclein. In such an embodiment, the nucleobase oligomer may include the sequence AAGGAATTCATTAGCCATGGATGTA (SEQ ID NO:1). In certain embodiments, a suitable nucleobase oligomer may target a human β-synuclein. In such an embodiment, the nucleobase oligomer may include the sequence GAGTGGGGCCGCCAGGATGGACGTG (SEQ ID NO:2). In certain embodiments, a suitable nucleobase oligomer may target a human γ-synuclein. In such an embodiment, the nucleobase oligomer may include the sequence ACCCTGCACACCCACCATGGATGTC (SEQ ID NO:3).

A nucleobase oligomer may be capable of hybridizing to the start codon of a target transcript. In such embodiments, the nucleobase oligomer may be capable of hybridizing to one or more nucleotides of the start codon. The nucleobase oligomer may additionally be capable of hybridizing to one or more nucleotides 3' of the start codon, one or more nucleotides 5' of the start codon, or both. In certain embodiments, the nucleobase oligomer is a phosphorodiamidate morpholino oligomer.

Treatment of spinal cord injury or traumatic brain injury with a nucleobase oligomer may improve survival of neurons, regeneration of neurons, or other outcomes in both cells that are likely to die as a result of injury (e.g., neurons likely to die) and/or cells that are likely to survive injury (e.g., neurons that are likely to survive). Distinct cell types or groups of cells may respond to treatment with a nucleobase oligomer with varying efficacy or varying responses. Treatment outcomes may also be observed at the systemic or organism level, including some aspects of functional recovery.

As described herein, synuclein knockdown by a nucleobase oligomer may increase neuronal survival after spinal cord injury. Knockdown of synuclein following spinal cord injury improves neuronal survival in both neurons that are likely to die as a result of spinal cord injury and those that are not likely to die as a result of spinal cord injury.

Synuclein knockdown may increase axonal sprouting and regeneration. The increased numbers of axons may be observed both proximal and distal to a site of injury, indicating that synuclein knockdown may increase axon sprouting above the lesion, as well as axon regeneration below the lesion. Increased axon sprouting and regeneration may be a mechanism by which functional outcomes of spinal injury may be improved, as supported by observations of spontaneous axon sprouting and regeneration after spinal cord injury in vertebrates ranging from lampreys to mammals. These neurons may be synaptically connected within the spinal cord; synaptic connections may form in a manner such that the neurons are capable of normal physiological responses.

In certain embodiments a nucleobase oligomer contemplated herein may effectively treat spinal cord injury when a subject is treated within 1 week or less to within 11 weeks or more after injury. Treatment within 11 weeks of injury or longer may result in decreased synuclein accumulation or aggregation. Untreated subjects have been found to spontaneously down-regulate synuclein mRNA levels between 1 and 11 weeks following spinal cord injury. These data may suggest a mechanism of synuclein regulation, perhaps evolved to counter synuclein accumulation or aggregation. Nevertheless, synuclein protein accumulates over the same period in these animals.

The efficacy of post-injury treatment with translation-blocking synuclein nucleobase oligomers suggests that new protein synthesis may contribute to synuclein accumulation and aggregation. Synuclein proteins may also be subject to dynamic turnover. Synuclein present in aggregates may be subject to dynamic turnover. Mechanisms of reducing synuclein accumulation and aggregation therefore include at least treatment with anti-synuclein nucleobase oligomers that decrease the production of synuclein and treatments that inhibit or reverse aggregate formation.

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In some embodiments, a nucleotide oligomer is an open linear structure. In certain embodiments, the ends of a linear polymeric structure can be further joined to form a circular structure. Within the oligonucleotide structure, the phosphate groups are commonly referred to as forming the backbone of the oligonucleotide. The normal linkage or backbone of RNA and DNA is a 3' to 5' phosphodiester linkage.

A variety of nucleobase oligomers capable of inhibiting expression of a target are known in the art. Illustrative nucleobase oligomers include oligonucleotides capable of inhibiting accumulation or aggregation of synuclein, Aβ, or Tau.

At least two types of oligonucleotides induce cleavage of one or more target RNA molecules by RNase H: polydeoxynucleotides with phosphodiesters (PO) and oligonucleotides with phosphorothioate (PS) linkages. Alternatively, certain nucleobase oligomers may not induce RNase H. For example, 2'-OMe-RNA sequences are not substrates for RNase H.

In particular embodiments, a nucleobase oligomer may be based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide.

Methods and reagents of the present invention may be used in conjunction with any technologies that may be developed, including covalently-closed multiple antisense (CMAS) oligonucleotides, ribbon-type antisense (RiAS) oligonucleotides, and large circular antisense oligonucleotides. Examples of these and related technologies are known in the art.

In certain embodiments a nucleobase oligomer suitable for the methods described herein may be an oligonucleotide including a modified backbone or one or more non-natural internucleoside linkages. A nucleobase oligomer having a modified backbone may be a nucleobase oligomer that retains a phosphorus atom in the backbone or a nuclease oligomer that does not have a phosphorus atom in the backbone. A nucleobase oligomer may also be a modified oligonucleotide that does not have a phosphorus atom in its internucleoside backbone.

A nucleobase oligomer having a modified oligonucleotide backbone may include, e.g., a backbone modified to include phosphorothioates, chiral phosphorothioates, phosphorodithioates, phosphotriesters, aminoalkyl-phosphotriesters, methyl and other alkyl phosphonates (e.g., 3'-alkylene phosphonates and chiral phosphonates), phosphinates, phosphoramidates (e.g., 3'-amino phosphoramidate and aminoalkylphosphoramidates), thionophosphoramidates, thionoalkylphosphonates, thionoalkylphosphotriesters, boranophosphates having normal 3'-5' linkages, 2'-5' linked analogs of boranophosphates, and boranophosphates having inverted polarity, such that adjacent pairs of nucleoside units are linked 3'-5' to 5'-3' or 2'-5' to 5'-2'. Techniques for the preparation of phosphorus-containing linkages are known in the art.

A nucleobase oligomer having a modified oligonucleotide backbone may include, e.g., a backbone that does not include a phosphorus atom may have a backbone that includes one or more short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Techniques for the preparation of oligonucleotides are known in the art.

In certain embodiments a nucleobase oligomer suitable for use in the methods described herein may be a morpholino. Morhpolinos are known in the art. A morhpolino may be a nucleobase oligomer having one or more nucleobase linked to a 6-membered morpholine ring. In particular embodiments, one or more, or all nucleobases, of a nucleobase oligomer may be linked to morpholine rings, e.g. morpholine rings linked by phosphorodiamidate linkages. Morpholine rings of a morpholinos may be linked phosphorodiamidate linkages. In particular embodiments, one or more or all of the eight or more consecutive nucleobases capable of hybridizing to a target RNA may be linked to morpholine rings, e.g. morpholine rings linked by phosphorodiamidate linkages.

In certain embodiments, both the sugar and the internucleoside linkage, i.e., the backbone, of a nucleobase oligomer of the present invention may be replaced, while the nucleobase units may be maintained for target recognition. A Peptide Nucleic Acid (PNA) may be an example of such a nucleobase oligomer. In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are known in the art.

In certain embodiments a nucleobase oligomer suitable for the methods described herein may include one or more nucleobase modifications or substitutions. An "unmodified" or "natural" nucleobase means a nucleobase selected from the purine bases, adenine (A) and guanine (G), or the pyrimidine bases: thymine (T), cytosine (C) and uracil (U). Any other nucleobase, synthetic or natural, is a modified nucleobase. Examples of modified nucleobases include 5-methylcytosine (5-me-C), 5-hydroxymethyl cytosine, xanthine, hypoxanthine, 2-aminoadenine, 2-propyl adenine, 2-propyl guanine, 6-methyl adenine, 6-methyl guanine, other alkyl derivatives of adenine and guanine, 2-thiouracil, 2-thiothymine, 2-thiocytosine, 5-halouracil, 5-halocytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-thiol, 8-thioalkyl, 8-thydroxyl, other 8-substituted adenines and guanines, 5-halo (e.g., 5-bromo) uracil, 5-halo (e.g., 5-bromo) cytosine, 5-trifluoromethyl uracil, 5-trifluoromethyl cytosine, other 5-substituted uracils and cytosines, 7-methylguanine, 7-methyladenine, 8-azaguanine, 8-azaadenine, 7-deazaguanine, 7-deazaadenine, 3-deazaguanine, 3-deazaadenine. Further nucleobases include those disclosed in U.S. Pat. No. 3,687,808, The Concise Encyclopedia Of Polymer Science And Engineering, pp. 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pp. 289-302, Crooke, S. T. and Lebleu, B., ed., CRC Press, 1993. Certain of these modified or substituted nucleobases increase the binding affinity of an antisense oligonucleotide its target as compared to an unmodified nucleobase oligonucleotide having the same target. These include 5-substituted pyrimidines, 6-azapyrimidines, and N-2, N-6 and O-6 substituted purines, e.g., 2-aminopropyladenine, 5-propynyluracil and 5-propynylcytosine. 5-methylcytosine substitutions have been shown to increase nucleic acid duplex stability by 0.6-1.2° C. In particular embodiments, one or more of these base substitutions may be combined with 2'-O-methoxyethyl or 2'-O-methyl sugar modifications. Techniques for the preparation of certain of the above noted modified nucleobases as well as other modified nucleobases are known in the art.

In certain embodiments the nucleobase oligomers may be chemically linked to one or more moieties or conjugates that enhance the activity, cellular distribution, or cellular uptake of the nucleobase oligomer. Moieties that may be chemically linked to a nucleobase oligomer of the present invention include but are not limited to lipid moieties such as a cholesterol moiety, cholic acid, a thioether (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, adamantane acetic acid, a palmityl moiety, or an octadecylamine or hexylamino-carbonyl-oxycholesterol. These and other chemical linkages that may be included in a nucleobase oligomer are known in the art.

A nucleobase oligomer of the present invention may be a chimeric compound. Chimeric nucleobase oligomers typically contain at least one region where the nucleobase oligomer is modified to in order to increase resistance of the nucleobase oligomer to nuclease degradation, increase cellular uptake of the nucleobase oligomer, and/or increased the binding affinity of the nucleobase oligomer for a target nucleic acid. In some instances, a separate region of the nucleobase oligomer may be constructed to serve as a substrate for enzymes capable of cleaving RNA:DNA or RNA:RNA hybrids. For example, RNase H is a cellular endonuclease capable of cleaving the RNA strand of RNA:DNA duplexes. Activation of RNase H may result in cleavage of an RNA target, enhancing the efficiency with which a nucleobase oligomer inhibits target expression. Consequently, when the efficiency of target knockdown is enhanced by a chimeric nucleobase oligomer, a nucleobase oligomer of a given length may knock down a target with efficiency comparable to that expected of a comparatively longer phosphorothioate deoxyoligonucleotide capable of hybridizing to the same target region as the chimeric nucleobase oligomer. Chimeric nucleobase oligomers of the invention may be formed as composite structures of two or more nucleobase oligomers. In some instances, a nucleobase oligomer formed as a composite structure of two or more nucleobase oligomers may be an oligonucleotide; such oligonucleotide chimeras may be referred to as hybrids or gapmers. The preparation of such hybrid structures is known in the art.

In particular embodiments, one or more nucleobase oligomers may be synthesized through the well-known technique of solid phase synthesis. Equipment for such synthesis is sold by several vendors including, for example, Applied Biosystems (Foster City, Calif.). Any other means for such synthesis known in the art may additionally or alternatively be employed for synthesis of one or more nucleobase oligomers of the present invention. Similar techniques may be used to prepare oligonucleotides such as phosphorothioate oligonucleotides and alkylated derivatives.

In certain embodiments the nucleobase oligomers described herein may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Techniques and reagents for the preparation of uptake, distribution and/or absorption assisting formulations are known in the art.

Locked nucleic acids (LNAs) contain a 2'O, 4'-C methylene bridge that restricts the flexibility of the ribofuranose ring of the nucleotide analog and locks it into the rigid bicyclic N-type conformation. LNAs show improved resistance to certain exo- and endonucleases, activate RNAse H, and can be incorporated into almost any nucleobase oligomer. Accordingly, in certain embodiments, the nucleobase oligomer(s) used in the methods described herein may include one or more LNAs.

LNA-containing nucleobase oligomers can be prepared using standard phosphoramidite synthesis protocols. Additional details regarding LNAs can be found in International Publication Number WO99/14226 and U.S. Patent Publication Number US 2002/0094555 A1, each of which is hereby incorporated by reference.

Arabinonucleic acids (ANAs) are nucleobase oligomers based on D-arabinose sugars instead of the natural D-2'-deoxyribose sugars. The binding affinity of underivatized ANA analogs for RNA is similar to that of phosphorothioates. When the arabinose sugar is derivatized with fluorine (2' F-ANA), an enhancement in binding affinity results. Formation of ANA/RNA and F-ANA/RNA duplexes may result in efficient selective hydrolysis of bound RNA. ANA analogs can be stabilized in cellular media by a derivatization at their termini with simple L sugars. A nucleobase oligomer of the present invention may include one or more ANAs. The use of ANAs in therapy is known in the art.

Formulation and Administration of Nucleobase Oligomers

In some instances, delivery of a naked nucleobase oligomer may be sufficient to inhibit expression of a target protein in a cell. In other embodiments, pharmaceutical formulations may enhance delivery or efficacy of a nucleobase oligomer to cells, e.g., a cell present in a subject.

Nucleobase oligomers described herein may be used to form pharmaceutical compositions. In various embodiments one or more nucleobase oligomer(s) described herein can be administered within a pharmaceutically-acceptable diluent, carrier, or excipient. In certain embodiments the nucleobase oligomer(s) may be administered in unit dosage form. Conventional pharmaceutical practice may be employed to provide suitable formulations or compositions for administration to subjects (e.g., humans or non-human mammals).

The pharmaceutical compositions comprising nucleobase oligomers described herein can be administered in a number of ways, e.g., depending upon the area to be treated and whether the treatment is to be applied locally or systemically. Administration may be topical (e.g. by ophthalmic delivery, delivery to mucous membranes, vaginal delivery, or rectal delivery), pulmonary (e.g., by inhalation of a powder or aerosol, insufflation of a powder or aerosol, use of a nebulizer, intratracheal delivery, intranasal delivery, epidermal delivery, or transdermal delivery), oral, or parenteral. Parenteral administration includes, inter alia, intravenous, intraarterial, subcutaneous, intraperitoneal, or intramuscular injection or infusion; as well as intracranial delivery, e.g., intrathecal or intraventricular delivery.

Any appropriate route of administration may be employed. For example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. In particular embodiments, a therapeutic formulation of the present invention may be in the form of a liquid, solution, or suspension. Formulations for oral administration may be in the form of tablets or capsules. Formulations for intranasal formulations may be in the form of powders, nasal drops, or aerosols. The preparation of pharmaceutical formulations is well known in the art (see, e.g., *Remington: The Science and Practice of Pharmacy.* $22^{nd}$ ed. Ed. L. V. Allen, Jr. London: Pharmaceutical Press, 2012).

Formulations for parenteral administration may, for example, contain excipients, sterile water, or saline, polyalkylene glycols such as polyethylene glycol, oils of vegetable origin, or hydrogenated napthalenes. Certain parenteral formulations of the present invention may be formulated to control the release of a nucleobase oligomer. A controlled release formation may include one or more biocompatible, biodegradable lactide polymer, lactide/glycolide copolymer, or polyoxyethylene-polyoxypropylene copolymers. Other potentially useful parenteral delivery systems may include ethylene-vinyl acetate copolymer particles, osmotic pumps, implantable infusion systems, and liposomes. Formulations for inhalation may contain excipients, e.g., lactose, or may be aqueous solutions containing, e.g., polyoxyethylene-9-lauryl ether, glycocholate, or deoxycholate. Formulations for inhalation may be oily solutions for administration in the form of nasal drops, or as a gel.

Nucleobase oligomers formulations contemplated herein include, but are not limited to any pharmaceutically acceptable salts, esters, salts of such esters, and/or any other compound that, upon administration to an animal, is capable of providing (directly or indirectly) the nucleobase oligomer(s). Accordingly, for example, the disclosure is also drawn to prodrugs and pharmaceutically acceptable salts of the compounds of the invention, pharmaceutically acceptable salts of such prodrugs, and other bioequivalents.

Also contemplated herein are therapeutic agents that are prepared as a prodrug of a nucleobase oligomer. In certain particular embodiments, prodrug versions of the oligonucleotides of the invention can be prepared as SATE ((S-acetyl-2-thioethyl) phosphate) derivatives according to methods disclosed in the art.

In various embodiments pharmaceutically acceptable salts of nucleobase oligomers are contemplated. Pharmaceutically acceptable base addition salts are formed with metals or amines, such as alkali and alkaline earth metals or organic amines. Examples of metals used as cations may include sodium, potassium, magnesium, calcium, and the like. Examples of suitable amines may include N,N'-dibenzylethylenediamine, chloroprocaine, choline, diethanolamine, dicyclohexylamine, ethylenediamine, N-methylglucamine, and procaine. The base addition salts of acidic compounds may be prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

A pharmaceutical addition salt may be a pharmaceutically acceptable salt of an acid form of a composition of the present invention or a component of a composition of the compositions of the present invention. Pharmaceutical addition salts include organic and inorganic acid salts of the amines. Acid salts include the hydrochlorides, acetates, salicylates, nitrates and phosphates. Other pharmaceutically acceptable salts are known in the art. Pharmaceutically acceptable salts include basic salts of a variety of inorganic and organic acids, such as salts of inorganic acids (e.g. hydrochloric acid, hydrobromic acid, sulfuric acid or phosphoric acid), organic carboxylic acid, sulfonic acid, sulfo acids, phospho acids or N-substituted sulfamic acids (e.g., acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid). Pharmaceutically acceptable salts include basic salts with amino acids, such as the 20 alpha-amino acids involved in the synthesis of proteins in nature (e.g., glutamic acid or aspartic acid), phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or other acid organic compounds (e.g., ascorbic acid). Pharmaceutically acceptable salts may also be prepared with a pharmaceutically acceptable cation. Suitable pharmaceutically acceptable cations are known in the art and include alkaline, alkaline earth, ammonium and quaternary ammonium cations. Carbonates or hydrogen carbonates are also possible.

For oligonucleotides and other nucleobase oligomers, suitable pharmaceutically acceptable salts may include (i) salts formed with cations such as sodium, potassium, ammonium, magnesium, calcium, polyamines (e.g., spermine or spermidine), etc.; (ii) acid addition salts formed with inorganic acids such as hydrochloric acid, hydrobromic acid, sulfuric acid, phosphoric acid, nitric acid and the like; (iii) salts formed with organic acids such as acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methane sulfonic acid, p-toluenesulfonic acid, naphthalenedisulfonic acid, polygalacturonic acid, and the like; and (iv) salts formed from elemental anions such as chlorine, bromine, and iodine.

Formulations of a nucleobase oligomer may be administered to human patients (or, e.g., in veterinary applications, to non-human mammals) in therapeutically effective amounts (e.g., amounts which prevent, eliminate, or reduce a pathological condition) to provide therapy for a disease or condition. The preferred dosage of a nucleobase oligomer of the invention is likely to depend on such variables as the type and extent of the disorder, the overall health status of the particular patient, the formulation of the compound (e.g., the chemical composition of the nucleobase oligomer; e.g., the inclusion of excipients), and its route of administration.

A nucleobase oligmer pharmaceutical composition may be administered in a single or in multiple administrations depending on the dosage, the required frequency of administration, and the known or anticipated tolerance of the subject for the pharmaceutical composition with respect to dosages and frequency of administration. In various embodiments, the composition may provide a sufficient quantity of a nucleobase oligomer of the present invention to effectively treat one or more symptoms of spinal cord injury or traumatic brain injury in a subject.

In some embodiments, a nucleobase oligomer may be administered within one week of a spinal cord injury or traumatic brain injury. In particular embodiments, a nucleobase oligomer may be administered within 3 days (72 hours) of a spinal cord injury or traumatic brain injury. In still more particular embodiments, a nucleobase oligomer may be administered within 1 day (24 hours) of spinal cord injury or traumatic brain injury.

In certain embodiments, administration of a nucleobase oligomer of the described herein may be oral. In certain embodiments, administration of a nucleobase oligomer described herein may be parenteral. Parenteral administration may include intraspinal, intrathecal, epidural, subdural, subcutaneous, or intravenous administration. In particular embodiments, parenteral administration may include a subcutaneously implanted device. Means of parenteral administration are known in the art.

In certain therapeutic or prophylactic applications, a nucleobase oligomer described herein may be administered to a mammal, e.g., a human, such as a human diagnosed as having or determined to be at risk of spinal cord injury or traumatic brain injury, or to a non-human mammal, to prophylactically and/or therapeutically inhibit accumulation or aggregation of synuclein, and/or Aβ, and/or Tau aggregation, and/or to slow the onset, and/or to slow the progression, and/or to mitigate one or more symptoms of a spinal cord injury and/or traumatic brain injury, where such symptoms including but are not limited to synuclein aggregation, and/or A13 aggregation, and/or Tau aggregation.

The pharmaceutical compositions described herein may be suitable for administration to an animal, e.g., for veterinary use. Certain embodiments of the present invention may include administration of a pharmaceutical composition of the present invention to a non-human organism, e.g., a non-human primates, canine, equine, feline, porcine, ungulate, or lagomorphs organism or other vertebrate.

Treatments with a nucleobase oligomer described herein can be combined with other therapies for the treatment of amyloidogenic conditions or conditions associated with neuronal damage, such as spinal cord injury. In some embodiments, combinatorial treatment involving a nucleobase oligomer as described herein and a known treatment of an amyloidogenic condition may result in treatment synergy.

EXAMPLES

The following examples are offered to illustrate, but not to limit the claimed invention.

Spinal cord injury or traumatic brain injury may cause widespread damage to neurons, often resulting in neuronal death. Substantial death of neurons limits regeneration and recovery. In mammals, loss of neurons and poor capacity for axon and synapse regeneration may contribute to permanent impairment of movement or sensation after spinal cord injury. The large size of giant reticulospinal (RS) neurons in the brain of the lamprey, *Petromyzon marinus* provides a model for the study of neurodegeneration and death following spinal cord injury.

Example 1: Reducing Synuclein Accumulation after Spinal Cord Injury Improves Neuronal Survival and Axon Regeneration Spinal cord injury (SCI) causes substantial neuronal death, thereby limiting regeneration and recovery. While strategies for improving axon regeneration are becoming clear, much less is known about how to promote the survival of damaged neurons. Here, we take advantage of the giant reticulospinal neurons in lamprey brain, that permit studies of post-injury neuronal responses at the level of individual neurons. Using imaging approaches, we identify synuclein accumulation as a key factor limiting neuronal survival after SCI. We show that post-injury synuclein accumulation is greatly reduced after application of the "molecular tweezer" inhibitor, CLR01, or a translation-blocking morpholino. Consequently, reduction of synuclein accumulation/aggregation not only spared neurons, but also enhanced axon sprouting and regeneration. Thus, reducing synuclein aggregation is a novel strategy for improving regeneration after SCI.

Materials and Methods

Spinal Cord Transections and Drug Application

Larval lampreys (*Petromyzon marinus*; 10-13 cm) were anesthetized in 0.1 g/L MS-222 (Argent Labs). Then, the spinal cord was transected at the $5^{th}$ gill, as previously described (Busch and Morgan, 2012). CLR01 (2.4 µg) or vehicle (lamprey internal solution: 180 mM KCl, 10 mM HEPES, pH 7.4) was added at the time and site of spinal injury via Gelfoam. 3'-Lissamine labeled morpholinos (10 µg; GeneTools, Inc.) were applied similarly. These included a translation-blocking synuclein morpholino (Syn MO) (5'-CGC GTC CAT TCC TCT TTC TTT GTC T-3', (SEQ ID NO:4)) generated against the start site of lamprey γ-synuclein (NCBI Accession #JN544525.1), a five base pair mismatch synuclein morpholino (MM MO) (5'-CGC cTg CAT TgC TCT TTg TTT cTC T-3', (SEQ ID NO:5)), and the standard control morpholino (Con MO) (5'-CCT CTT ACC TCA GTT ACA ATT TAT A-3', (SEQ ID NO:6)). Afterwards, lampreys were allowed to recover at room temperature for 11 weeks. Next, lampreys were re-anesthetized, and the brains and spinal cords were dissected out for further experimentation by a researcher blinded to the experimental conditions. All procedures were approved by the Institutional Animal Care and Use Committees at UT-Austin and MBL in accordance with NIH standards.

Immunofluoresence and Image Analysis

Brains and spinal cords were fixed in 4% paraformaldehyde in 0.1 M PBS, pH 7.4. Immunofluoresence staining of whole mounted brains and cryosectioned spinal cords was done as previously described (Busch and Morgan, 2012; Jin et al., 2009). Primary antibodies included a polyclonal pan-synuclein antibody (1:100 dilution; Abcam; ab6176) and a monoclonal neurofilament-180 antibody (1:100; LCM16; kind gift from Dr. Michael Selzer), which were previously characterized (Busch and Morgan, 2012; Jin et al., 2009). The secondary antibody was ALEXAFLUOR® 488-conjugated goat anti-rabbit IgG (1:300; Life Technologies). Nuclei were stained with PROLONG® Gold with DAPI.

Synuclein immunofluorescence in the giant neurons was imaged using a Zeiss laser scanning confocal on an Axioskop 2FS microscope (10× objective; 0.3 NA EC Plan-Neofluar). Z-stacks of images were acquired, from which 3D projections were generated. For quantification of fluorescence levels, images were acquired under identical conditions. Fluorescence intensity associated with each giant RS neuron was measured in ImageJ, followed by background subtraction. Data were averaged from n=6-13 lamprey brains.

NF-180 immunofluorescence and DAPI staining were imaged from spinal cord sections using an EVOS® FL Cell Imaging System (10×, 0.3 NA and 20×, 0.5 NA Plan-Fluorite objectives). Distances proximal, within, and distal to the lesion were sampled. For the axon regeneration analysis, all NF-180-labeled axons in the ventral half of the spinal cord were counted and averaged from n=4-8 animals per condition.

Nissl Staining and Image Analysis

After completing the synuclein immunofluorescence analysis, lamprey brains subsequently underwent Nissl staining, as previously described (Busch and Morgan (2012) *J. Comp. Neurol.* 520: 1751-1771). Low-magnification images of whole lamprey brains were acquired either with a DFC420C camera connected to a Leica MZ10F stereoscope or an AxioCam MRc camera connected to a Zeiss SteREO Discovery V20. High-magnification images were acquired either with a Leica DMI 4000B microscope (HC PL Fluotar 10×/0.3 NA objective) or the SteREO Discovery V20 (PlanApo S 2.3×FWD 10 mm, 70 magnification). Nissl intensity associated with each giant neuron was measured, followed by background subtraction from the adjacent neuropil. Neurons that exhibited Nissl intensities greater than 0 were categorized as "Nissl (+)". All statistics and graphs in this study were generated using Origin Pro.

Generation of Recombinant γ-Synuclein and Aggregation Analysis In Vitro.

After purification of GST-tagged lamprey γ-synuclein, GST was cleaved off using thrombin (10 U/mg protein; GE Healthcare). Untagged γ-synuclein was then separated from GST and thrombin using Glutathione Sepharose 4B beads and p-aminobenzamidine agarose (100 pl/50 U thrombin; Sigma A7155), respectively, and dialyzed into 0.1M PBS, pH 7.4. Aggregation of the purified lamprey γ-synuclein was analyzed using the thioflavin T (ThT) fluorescence assay and electron microscopy as described previously (Roychaudhuri et al. (2014) *J. Mol. Biol.* 426: 2422-2441), except that 100 pM synuclein and varying CLR01 concentrations were used.

Results.

CLR01 Reduces Post-Injury Synuclein Accumulation.

We took advantage of the identified giant reticulospinal (RS) neurons of lamprey to examine the relationship between post-injury synuclein accumulation and neuronal death. Lamprey brains possess ~30 identified giant RS neurons, which are bilaterally localized to stereotypical positions in the midbrain and hindbrain (FIG. 1, panel A). These are the mesencephalic (M), isthmic (I), and bulbar (B) Muller cells, and the Mauthner (Mth) cells (Rovainen (1967) *J. Neurophysiol.*, 30: 1000-1023). Spinal cord transection severs the axons of all giant RS neurons (FIG. 1, panel A), after which a reproducible subset degenerates, as demonstrated by a loss of Nissl substance and/or a gain of signal for FluoroJadeC®, TUNEL, and activated caspases (Barreiro-Iglesias and Shifman (2012) *Enzyme Res.*, 2012: 835731; Busch and Morgan (2012) *J. Comp. Neurol.* 520: 1751-1771; Shifman et al. (2008) *J. Comp. Neurol.* 510: 269-282). In contrast, another subset survives and regenerates their axons, as demonstrated by strong Nissl staining or retrograde labeling from axons (Id.). We call these classes of neurons "poor survivors" and "good survivors," respectively (FIG. 1, panel A).

Immunostaining for synuclein revealed low and diffuse levels within the giant neurons of uninjured, control lampreys (FIG. 1, panels B, D). In contrast, 11 weeks post-transection, "poor survivor" neurons, including M2, M3, I1, B3, and Mth, had selectively accumulated synuclein throughout their cell bodies, whereas "good survivors" did not (FIG. 1, panel C). Synuclein accumulation appeared in the form of small, punctae throughout the cytoplasm (FIG. 1, panel E). Quantitatively, synuclein immunofluorescence intensity remained low but slightly elevated in the "good survivors" after spinal injury (FIG. 1, panel F) (Control: 5.3±1.3 AU, n=6 animals, 108 cells; Transected: 9.3±1.5 AU, n=10 animals, 180 cells; T-test; p=0.07). "Poor survivors" exhibited a 4.5-fold increase in synuclein immunofluorescence intensity (FIG. 1, panel F) (Control: 10.2±2.6 AU, n=6 animals, 72 cells; Transected: 45.5±3.0 AU, n=10 animals, 119 cells; T-test; p=$4.2 \times 10^{-14}$). Thus, post-injury synuclein accumulation occurred predominantly in "poor survivors", corroborating a major observation from our previous study (Busch and Morgan, 2012). Neurons with synuclein aggregates are those that exhibit signs of degeneration (see FIGS. 2, panel I, and 3, panel I) (Busch and Morgan (2012) *J. Comp. Neurol.* 520: 1751-1771).

To address whether synuclein accumulation is causal for injury-induced neurodegeneration, we utilized the "molecular tweezer" CLR01 (FIG. 2, panel A), which inhibits α-synuclein self-assembly and toxicity in vitro (Acharya et al. (2014) *J. Biol. Chem.* 289: 10727-10737; Prabhudesai et al. (2012) *Neurotherapeutics,* 9: 464-476; Sinha et al. (2011) *J. Am. Chem. Soc.* 133: 16958-16969), and reduces neurodegeneration and improves survival in a zebrafish model of α-synuclein neurotoxicity (Prabhudesai et al., 2012).

Figure 2:
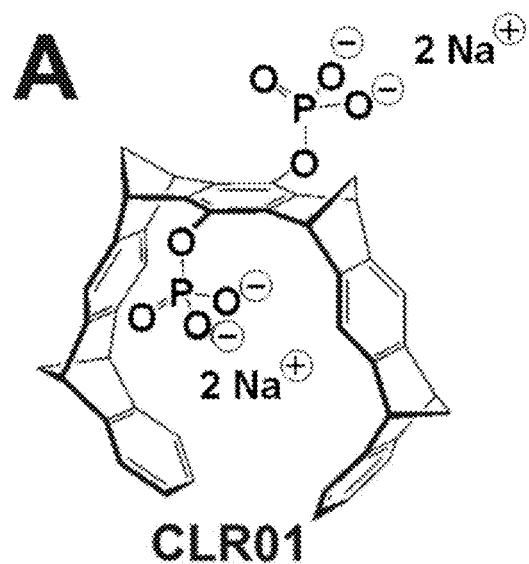
FIG. 2. CLR01, an inhibitor of synuclein aggregation, improves neuronal survival after spinal cord injury. Panel A: Structure of CLR01 and its effect on lamprey γ-synuclein aggregation, as measured by ThT fluorescence. Panels B-E: Confocal images of giant RS neurons showing that synuclein accumulation is greatly reduced after CLR01 treatment. Scale bar in panel C applies to panel B. Scale bar in panel E applies to panel D. Panel F: CLR01 significantly reduces synuclein levels in "poor survivors". Panels G-H: Nissl-stained brains from animals treated with vehicle (Control) or CLR01. With CLR01, there are fewer degenerating giant RS neurons, as indicated by loss of Nissl stain (red arrows), and more surviving neurons (white arrows). Scale bar in panel H applies to panel G. Panels I-J: Images showing Nissl staining (left) and synuclein immunofluorescence (right) from the same brains. Nissl (−) cells have high synuclein levels (red arrows). CLR01 increases the number of Nissl (+) neurons (white arrows). Scale bar in panel J applies to panel I. Panel K: Analysis showing effect of CLR01 treatment on individual RS neurons. Panel L: CLR01 significantly increases the number of Nissl (+) "poor survivor" neurons, as well as the number of Nissl (+) giant RS neurons within the entire population. Bars represent mean±S.E.M. (* $p<0.05$).
Figure 2:
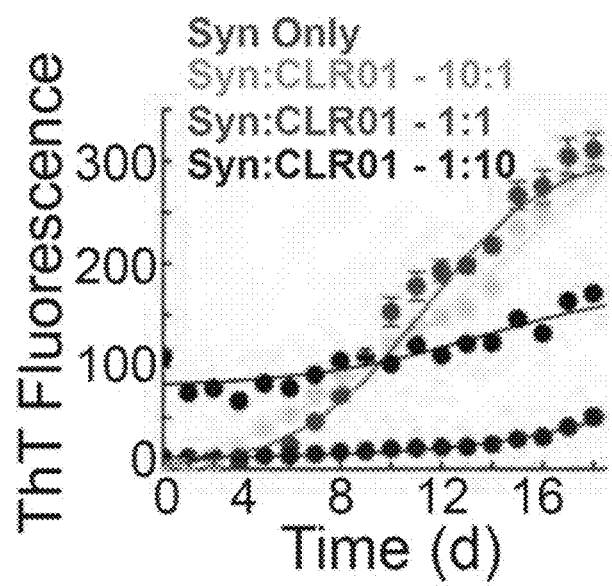

We tested first whether CLR01 inhibited self-assembly of recombinant lamprey γ-synuclein (GenBank: JN544525.1), the synuclein isoform expressed in giant neurons (Busch and Morgan (2012) *J. Comp. Neurol.* 520: 1751-1771). Full-length lamprey γ-synuclein shares 56% identity and 83% similarity with human α-synuclein. Similar to α-synuclein, lamprey γ-synuclein self-assembled into β-sheet-rich aggregates, as shown by an increase in ThT fluorescence, and this aggregation was inhibited by CLR01 in a dose-dependent manner (FIG. 2, panel A). Next, CLR01 (2.4 μg) or vehicle was applied to the spinal cord at the time and site of transection. Eleven weeks post-injury, synuclein accumulation was apparent in the "poor survivors" in vehicle-treated animals (FIG. 2, panels B, D), but was greatly reduced throughout the brain in CLR01-treated animals (FIG. 2, panel C), where levels remained low and diffuse throughout the soma (FIG. 2, panel E). Synuclein levels were statistically unchanged in "good survivors" of CLR01-treated animals, likely because initial levels of synuclein were low (FIG. 2, panel F) (Con: 5.0±1.1 AU, n=13 animals, 232 cells; CLR01: 5.6±1.3 AU, n=13 animals, 234 cells; T-test; p=0.7). In contrast, CLR01 significantly reduced synuclein levels in the "poor survivors" (FIG. 2F) (Con: 38.8±3.4 AU, n=13 animals, 154 cells; CLR01: 25.7±3.1 AU, n=13 animals, 156 cells; T-test; p=0.005). Thus, application of CLR01 is an effective strategy for reducing synuclein accumulation in neurons after spinal cord injury.

CLR01 Increases Neuronal Survival

To determine whether synuclein aggregation into toxic oligomers is causal for injury-induced neurodegeneration, we used Nissl staining to assay cell survival after CLR01 treatment. A dark blue, uniform Nissl staining marks healthy RS neurons [Nissl (+)], whereas degenerating neurons have little or no Nissl substance and appear swollen and chromalytic [Nissl (−)].

Multiple independent methods have confirmed that loss of Nissl staining reliably marks the degenerating RS neurons (Busch and Morgan (2012) *J. Comp. Neurol.* 520: 1751-1771; Shifman et al. (2008) *J. Comp. Neurol.* 510: 269-282). Eleven weeks post-injury, the brains of spinal-transected control animals exhibited many Nissl (−) neurons, indicating dead or dying cells (FIG. 2, panel G; red arrows). Nissl (−) neurons also exhibited synuclein accumulation (FIG. 2, panel I). In contrast, CLR01 treatment reduced Nissl (−) and increased Nissl (+) neurons, indicating greater neuronal survival (FIG. 2, panels H, J; white arrows). We performed a cell-by-cell analysis on vehicle-treated (n=13) and CLR01-treated animals (n=13), which provided a total population of 26 cells for each RS neuron type. The majority of giant RS neurons, including some "good survivors" and all "poor survivors," exhibited an increase in survival after CLR01 treatment, as shown by increased percentage of Nissl (+) staining (FIG. 2, panel K). Notably, CLR01 dramatically increased the percentage of Nissl (+) "poor survivors" more than 4-fold (FIG. 2L). Across the entire RS neuron population, CLR01 significantly increased neuronal survival by 22% (FIG. 2, panel L) (Con: 59.0±1.7 AU, n=13; CLR01: 72.1±3.1 AU, n=13; T-test; p=0.001). Taken together, CLR01 reduced synuclein accumulation and improved neuronal survival after spinal cord injury. This suggests that synuclein accumulation and aggregation promotes injury-induced neuronal death and that the deleterious effects of synuclein can be corrected by attenuating it's self-assembly.

Selective Knock Down of Synuclein Increases Neuronal Survival and Axon Regeneration.

To further assess the role of synuclein accumulation in injury-induced neurodegeneration, we used a translation-blocking synuclein morpholino (Syn MO) to inhibit synuclein production. As controls, we used a 5-base-pair mismatch synuclein morpholino (MM MO) and the standard control morpholino (Con MO). We show only the MM MO images due to space constraints.

Figure 3:
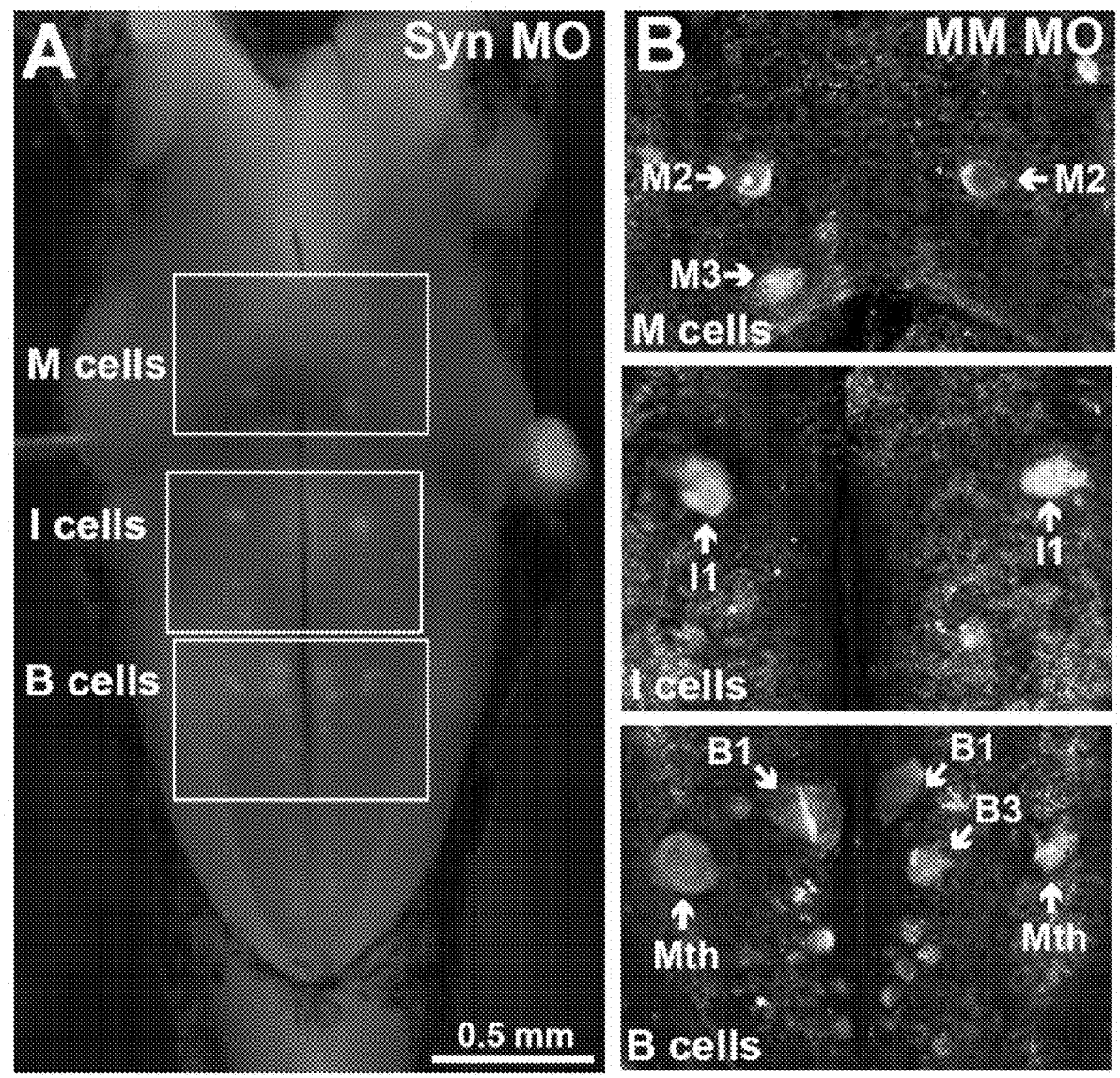
FIG. 3. Knockdown of synuclein production increases neuronal survival after injury. Panel A: Image of a lamprey brain. The synuclein morpholinos (red) have been retrogradely transported from the spinal lesion to the giant RS neurons where they remain up to 11 weeks post-injury. Panels B-E: Confocal images of giant RS neurons showing that synuclein accumulation is greatly reduced after synuclein morpholino (Syn MO) treatment, when compared to a mismatch morpholino (MM MO). Scale bar in panel C applies to panel B. Scale bar in panel E applies to panel D. Panel F: Syn MO significantly reduces synuclein levels in both "good" and "poor survivors". Con MO=standard control morpholino. Panels G-J: Compared to MM MO-treated animals, brains of lampreys treated with Syn MO exhibit fewer dying neurons (red arrows) and more surviving neurons (white arrows). Scale bar in panel H applies to panel G. Scale bar in panel J applies to panel I. Panels K-L: Synuclein knockdown improves survival of the giant RS neurons. Bars represent mean±S.E.M. (* $p<0.05$).

Fluorescently-labeled morpholinos were loaded at the time and site of spinal transection, after which they were retrogradely transported to the neuronal cell bodies (FIG. 3, panel A). Eleven weeks post-transection, synuclein accumulation still occurred in MM MO-treated animals (FIG. 3, panels B, D), but was greatly reduced after Syn MO treatment (FIG. 3C, E). Quantitatively, Syn MO significantly reduced synuclein immunofluorescence intensity in both good and poor survivors, compared to both controls (FIG. 3, panel F) (Good Survivors—Con MO: 25.7±1.9 AU, n=6 animals, 107 cells; MM MO: 26.0±2.4 AU, n=6 animals, 108 cells; Syn MO: 17.7±1.4 AU, n=8 animals, 140 cells; ANOVA; p=0.001; Poor Survivors—Con MO: 42.6±3.5 AU, n=6 animals, 72 cells; MM MO: 40.7±3.7 AU, n=6 animals, 72 cells; Syn MO: 26.5±2.5 AU, n=8 animals, 96 cells; ANOVA; p=2.9×10$^{-4}$). Similarly to CLR01, Syn MO reduced the number of degenerating neurons and increased the number of Nissl (+) neurons (FIG. 3, panels G-J). This positive effect on neuronal survival was observed in a subset of both good and poor survivors (FIG. 3, panel K). At the population level, SynMO significantly increased survival of the giant RS neurons, when compared to the Con MO treatment (Con MO: 56.7±5.7, n=6 animals; MM MO: 60.0±8.0, n=6 animals; Syn MO: 72.1±3.2, n=8 animals; ANOVA: p=0.13; post hoc ConMO/SynMO; p=0.03). The most dramatic effects of SynMO were observed in the "good survivor" subpopulation (FIG. 3, panel L). These data confirm that synuclein accumulation promotes injury-induced neurodegeneration. Further, the data indicate that reducing synuclein production is a second effective strategy for inhibiting synuclein accumulation and sparing neurons after SCI.

Figure 4:
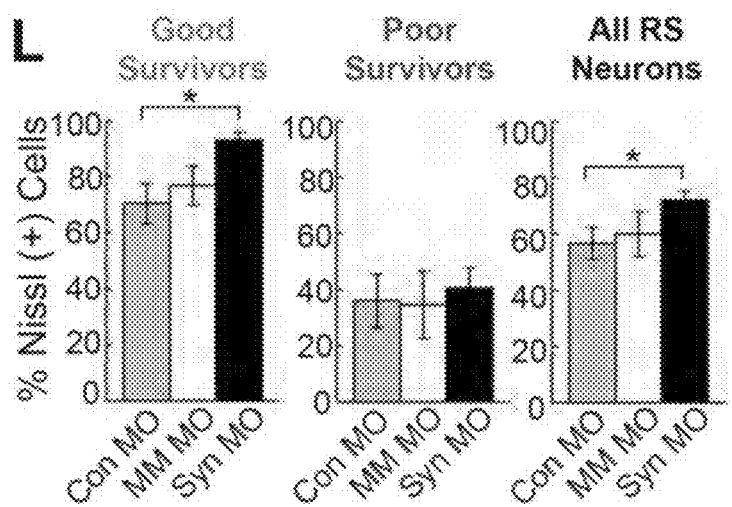
FIG. 4. Knockdown of synuclein increases axon regeneration after injury. Panel A: Cross-section of an uninjured, control spinal cord stained with toluidine blue, showing the positions of the axons from the giant Muller and Mauthner (Mth) neurons. D=dorsal; V=ventral. Panel B: Cryosection of a control spinal cord showing that NF-180 immunostaining of giant RS axons. Panels C-E: Cryosections of spinal cords at 11 weeks post-transection. Compared to untreated, transected (Trans) or MM MO-treated spinal cords, those treated with Syn MO exhibit substantially more NF-180 labeled axons. Scale bar in panel C applies to panels D-E. Panel F: Only the labeled axons in the ventral half of the spinal cord, containing the giant RS axons, were analyzed. Panel G: Syn MO significantly increases the number of NF-180-labeled ventral axons proximal, within, and distal to the spinal lesion. Bars represent mean±S.E.M. (* $p<0.05$).
Figure 4:
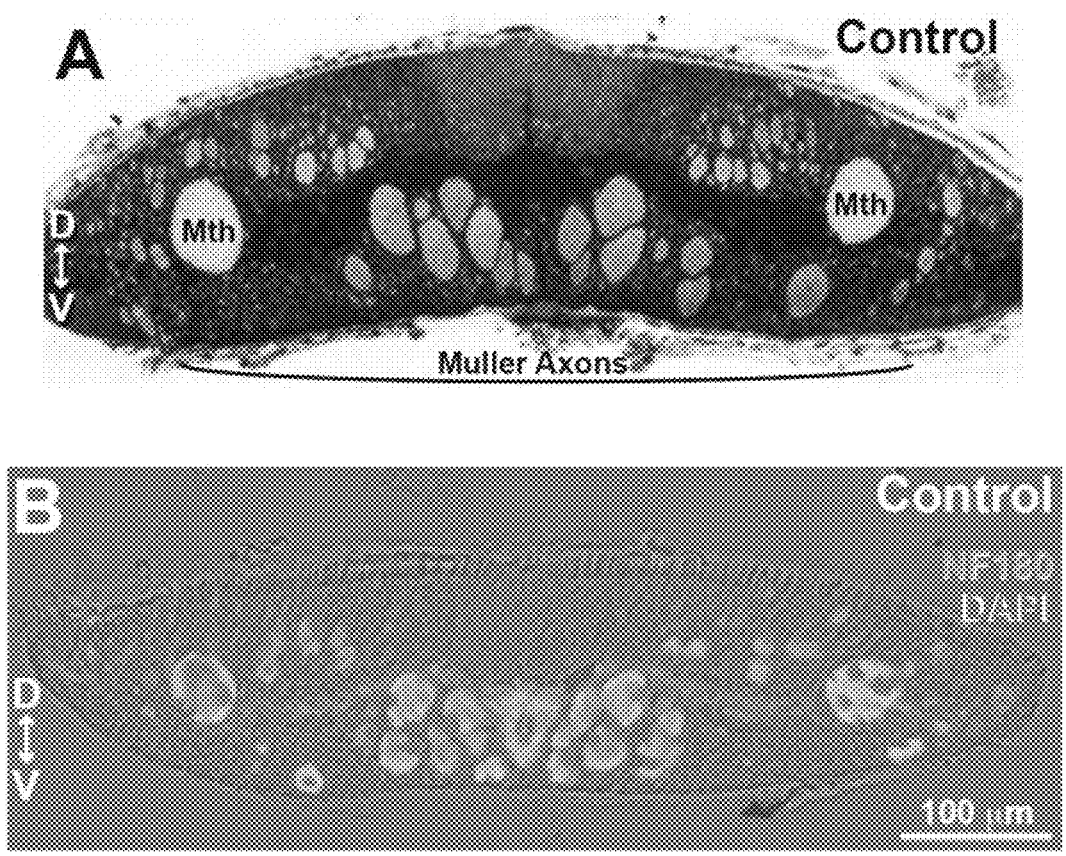

In view of the foregoing it was predicted that improved neuronal survival after synuclein knockdown may be accompanied by increased axonal regeneration. We therefore labeled and counted the number of large axons present in the ventromedial tract of the lamprey spinal cord. In uninjured control spinal cords, most giant RS axons are clustered in the ventromedial tract, though several others including Mauthner are positioned more laterally (FIG. 4, panel A). An antibody against lamprey neurofilament-180 (NF-180) reliably immunolabels all 30 giant RS axons (30.4±3.6 axons; n=5 spinal cords), and some sensory axons in the dorsal tract (FIG. 4, panel B). Eleven weeks post-injury, untreated transected spinal cords exhibited fewer NF-180 labeled axons proximal, within, and distal to the lesion site (FIG. 4, panel C). Quantification of NF180-labeled axons in the ventral half of the spinal cord (FIG. 4, panel F), corresponding to the giant RS neurons, revealed 13.4±3.0 large axons 448 μm distal to the lesion (FIG. 4, panel G). This number is commensurate with the expected 40-50% regeneration of giant RS axons previously observed (Oliphint et al. (2010) *J. Comp. Neurol.* 518: 2854-2872; Yin and Selzer (1983) *J. Neurosci.*, 3: 1135-1144). Transected spinal cords treated with MM MO had similar numbers of labeled axons at all distances (FIG. 4, panels D, G). In contrast, Syn MO significantly increased the number of labeled axons proximal, within, and distal to the lesion nearly 2-fold (FIG. 4, panels E, G), indicating that knockdown of post-injury synuclein production increased axon sprouting above the lesion site and regeneration through it.

Discussion.

This is the first demonstration in any experimental model that synuclein accumulation is causal for neurodegeneration and inhibits axon regeneration after SCI. Consequently, preventing synuclein self-assembly with CLR01, or reducing synuclein production using a translation-blocking morpholino, improved post-injury outcomes, including neuronal survival and axon regeneration. These findings demonstrate an advantage of lamprey giant RS neurons, where post-injury responses can be followed in individual, identified cells (Busch and Morgan (2012) *J. Comp. Neurol.* 520: 1751-1771; Shifman et al. (2008) *J. Comp. Neurol.* 510: 269-282). Interestingly, positive effects on neuronal survival were observed several months post-injury, though the CLR01 and morpholino treatments were only single-dose applications at the time of spinal injury. Thus, an exciting prospect is that early interventions preventing post-injury synuclein accumulation may have lasting effects that improve long-term outcomes after spinal cord injury.

Our findings in lampreys are believed to have applicability to other vertebrate models of spinal cord injury. Increased synuclein immunoreactivity has been reported in motor neurons of rabbits after spinal cord injury (Sakurai et al. (2009) *J. Cereb. Blood Flow Metab.* 29: 752-758) and in cortical axons of mice and humans after traumatic brain injury (Uryu et al. (2007) *Exp. Neurol.* 208: 185-192; Uryu et al. (2003) *Exp. Neurol.* 184: 214-224). Furthermore, increased levels of α-synuclein have been observed in the cerebral spinal fluid of TBI patients (Mondello et al. (2013) *Neurology*, 80: 1662-1668). We predict that increased synuclein immunoreactivity observed after injury in mammals is also due to synuclein aggregation in degenerating neurons. Reducing synuclein accumulation is believed to be a means to improve neuronal survival and regeneration. Proteins other than synuclein that are associated with neurodegenerative diseases, including tau, amyloid β-protein precursor, and amyloid β-protein (Aβ), are also elevated after nervous system injury in human and animals models (Johnson et al. (2010) *Nat. Rev. Neurosci.* 11: 361-370; Uryu et al. (2007) *Exp. Neurol.* 208: 185-192). These observations make CLR01 a particularly attractive therapeutic approach because it is a broad-spectrum inhibitor of protein self-assembly, and has been shown to reduce accumulation of Aβ and hyperphosphorylated tau in a mouse model of Alzheimer's disease (Attar et al. (2012) *Brain,* 135: 3735-3748).

Mechanistically, post-injury synuclein accumulation appears to be a dynamic process involving new protein synthesis. We previously showed that synuclein mRNA is spontaneously downregulated in the giant RS neurons between 1 and 11 weeks post-injury, but at the same time synuclein protein continues to accumulate, suggesting post-transcriptional mechanisms (Busch and Morgan (2012) *J. Comp. Neurol.* 520: 1751-1771). The fact that a translation-blocking synuclein morpholino succeeds in reducing post-injury synuclein accumulation indicates that the aggregates dynamically incorporate newly-synthesized protein. Consequently, drugs designed to reduce post-injury synuclein accumulation should reduce synuclein protein production and/or enhance its clearance in order to be effective. Accordingly, CLR01, which prevents α-synuclein aggregation in vitro and in vivo and facilitates α-synuclein clearance in vitro (Prabhudesai et al. (2012) Neurotherapeutics, 9: 464-476; Sinha et al. (2011) J. Am. Chem. Soc. 133: 16958-16969), reduced post-injury synuclein accumulation and improved neuronal survival.

In summary, we have identified synuclein accumulation as a target for therapeutic intervention for treating spinal cord injury. Given the growing number of molecular links between injury and disease, it is conceivable that synuclein-based treatments for Parkinson's Disease and other synucleinopathies will be applicable to spinal cord injury, and vice versa.

All publications, patent applications, and patents mentioned in this specification are herein incorporated by reference.

While the invention has been described in connection with the specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

What is claimed is:

1. A method of treating a subject having a spinal cord injury, said method comprising administering to said subject a molecular tweezers comprising the structure of CLR01:

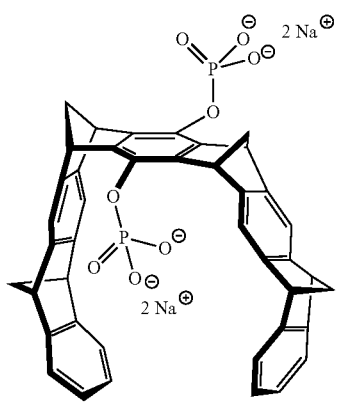

CLR01 wherein said molecular tweezers inhibits aggregation of synuclein protein in an amount sufficient to reduce aggregation and resulting cytotoxicity of said synuclein protein.

2. A method of treating a subject having a spinal cord injury, said method comprising administering to said subject a molecular tweezers comprising the structure of CLR01:

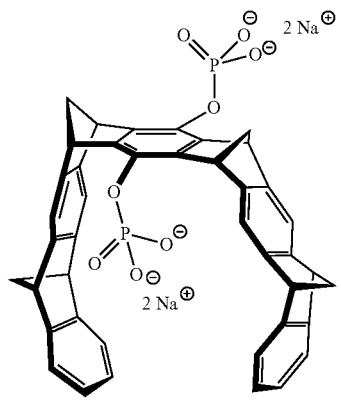

CLR01 wherein said molecular tweezers inhibits aggregation of a synuclein protein in an amount sufficient to ameliorate one or more symptoms of said spinal cord injury or traumatic brain injury.

3. The method of claim 2, wherein said amelioration comprises one or more responses selected from the group consisting of improved neuronal survival, improved neuronal regeneration, improvement/recovery of motor function, improvement/recovery of fine motor coordination, improvement/recovery from muscle spasticity, improvement/recovery from paresis or paralysis of one or both sides, reduction in severity and/or number of seizure disorders, improvement/recovery of balance, improvement/recovery of gait, improvement/recovery of cognitive function, improvement/recovery of perception, improvement/recovery of communication, improvement/recovery of reading and writing skills, improvement/recovery of planning, improvement/recovery of sequencing, improvement/recovery of judgment, improvement/recovery of sensory function, and/or amelioration of one or more deficits selected from the group consisting of impairment of sensation, impairment of motor function, dysfunction of the bowel, dysfunction of the bladder, sexual dysfunction, impairment of fertility, inability to effectively regulate blood pressure, impairment of thermoregulation, impairment of sweating, chronic pain, and impairment of involuntary functions.

4. The method of claim 2, wherein said method reduced neuron death.

5. The method of claim 2, wherein said method enhances axon sprouting and regeneration.

6. The method of claim 2, wherein said administration is via a means selected from the group consisting of parenteral administration, intraspinal administration, intrathecal or epidural administration, subdural administration, subcutaneous administration, intravenous administration, via a subcutaneously implanted device, and through a cannula.

* * * * *